(12) United States Patent
Bellail et al.

(10) Patent No.: US 11,731,985 B2
(45) Date of Patent: Aug. 22, 2023

(54) COMPOSITIONS AND METHODS FOR TREATING CANCER

(71) Applicant: Hb Therapeutics Inc., Indianapolis, IN (US)

(72) Inventors: Anita Bellail, Indianapolis, IN (US); Chunhai Hao, Indianapolis, IN (US); Ho Yin Lo, Bethel, CT (US)

(73) Assignee: Hb Therapeutics Inc., Indianapolis, IN (US)

( * ) Notice: Subject to any disclaimer, the term of this patent is extended or adjusted under 35 U.S.C. 154(b) by 255 days.

(21) Appl. No.: 17/054,118

(22) PCT Filed: May 8, 2019

(86) PCT No.: PCT/US2019/031245
§ 371 (c)(1),
(2) Date: Nov. 9, 2020

(87) PCT Pub. No.: WO2019/217509
PCT Pub. Date: Nov. 14, 2019

(65) Prior Publication Data
US 2021/0115064 A1    Apr. 22, 2021

Related U.S. Application Data

(60) Provisional application No. 62/669,640, filed on May 10, 2018.

(51) Int. Cl.
| | |
|---|---|
| C07D 277/82 | (2006.01) |
| C07D 417/04 | (2006.01) |
| C07D 217/26 | (2006.01) |
| C07D 277/68 | (2006.01) |
| C07D 417/12 | (2006.01) |
| C07D 513/04 | (2006.01) |
| A61K 31/428 | (2006.01) |
| A61K 31/429 | (2006.01) |
| A61P 35/00 | (2006.01) |
| C07C 275/40 | (2006.01) |
| C07D 217/06 | (2006.01) |
| C07D 277/64 | (2006.01) |

(52) U.S. Cl.
CPC ............ *C07D 513/04* (2013.01); *A61P 35/00* (2018.01); *C07C 275/40* (2013.01); *C07D 217/06* (2013.01); *C07D 277/64* (2013.01); *C07D 277/82* (2013.01); *C07D 417/04* (2013.01); *C07D 417/12* (2013.01)

(58) Field of Classification Search
CPC .. C07D 277/82; C07D 417/04; C07D 217/26; C07D 277/68; C07D 417/12; C07D 513/04; A61K 31/428; A61K 31/429; A61P 35/00
See application file for complete search history.

(56) References Cited

U.S. PATENT DOCUMENTS 4,088,768 A    5/1978  Paget et al.

FOREIGN PATENT DOCUMENTS

| KR | 101838615 B1 | 3/2018 |
|---|---|---|
| WO | 2001/057008 A1 | 8/2001 |
| WO | 2005/037845 A1 | 4/2005 |

OTHER PUBLICATIONS

Paget et al. (Journal of Medicinal Chemistry (1969), 12(5), 1016-18). Abstract.*
Harrouche et al. (European Journal of Medicinal Chemistry (2016), 115, 352-360). Abstract.*
Bellail, A.C. et al. "SUMO1 modification stabilizes CDK6 protein and drives the cell cycle and glioblastoma progression", 2014, Nature Communications, 5, Article No. 4234.
Caputo, R. et al. "Synthesis of benzothiazole derivatives and their biological evaluation as anticancer agents", 2012, Med. Chem. Res., 21, pp. 2644-2651.
Geiss-Friedlander, R. et al. "Concepts in sumoylation: a decade on", 2007, Nature Reviews: Molecular Cell Biology, 8, pp. 947-956.
Hay, R.T. "SUMO: A History of Modification", 2005, Molecular Cell, 18, pp. 1-12.
Seeler, J.S. et al. "SUMO and the robustness of cancer", 2017, Nature Reviews: Cancer, 17, pp. 184-197.
Song, E.Y. et al. "Synthesis of amide and urea derivatives of benzothiazole as Raf-1 inhibitor", 2007, European Journal of Medicinal Chemistry, Article In Press, pp. 1-6.
International Search Report, PCT/US2019/031245, dated Aug. 23, 2019.

* cited by examiner

*Primary Examiner* — Bruck Kifle
(74) *Attorney, Agent, or Firm* — Wiggin and Dana LLP

(57) ABSTRACT

The present invention relates to the field of anti-cancer compounds. More particularly, the invention relates to a family of benzothiazolyl urea or thiourea compound useful as such agents. The present invention also relates to methods for treating cancers using these compounds.

4 Claims, 16 Drawing Sheets

COMPOSITIONS AND METHODS FOR TREATING CANCER

CROSS-REFERENCE TO RELATED APPLICATIONS

This application is a national phase entry under 35 U.S.C. § 371 of International Application PCT/US2019/031245, filed May 8, 2019, which claims the benefit under 35 U.S.C. § 119(e) of U.S. Provisional Application No. 62/669,640 filed May 10, 2018, all of which are herein incorporated by reference in their entirety.

STATEMENT REGARDING FEDERALLY SPONSORED RESEARCH OR DEVELOPMENT

This invention was made with government support under Grant Number 1R43CA224461-01A1, awarded by the National Cancer Institute of the National Institutes of Health. The government has certain rights in the invention.

FIELD OF THE INVENTION

The present invention relates to the field of anti-cancer compounds. More particularly, the invention relates to a family of benzothiazolyl urea or thiourea compound useful as such agents. The present invention also relates to methods for treating cancers using these compounds.

BACKGROUND OF THE INVENTION

Cancer is a common cause of death worldwide. An unmet need remains for new and effective methods, systems, and compositions for the treatment of cancer. The etiology of and the biochemical pathways of cancer development and progression are complex, but represent a huge potential for the development of new targeted cancer therapies.

SUMO (small ubiquitin-like modifier) is a conserved member of the UB (ubiquitin) related protein family. See, Hay, R. T., SUMO: a history of modification. *Mol. Cell* 18, 1-12 (2005) and Geiss-Friedlander, R. and Melchior, F., Concepts in SUMOylation: a decade on. *Nat. Rev. Mai Cell Biol.* 8, 947-956 (2007). SUMO is a small regulatory protein that is linked to substrate proteins through enzymatic reactions. The cellular function of substrate proteins is controlled by SUMO conjugation.

The human genome encodes four SUMO isoforms named SUMO1, SUMO2, SUMO3, and SUMO4. It is unclear whether SUMO4 can be conjugated. SUMO2 and SUMO3 share about 97% amino acid homology and cannot be distinguished by any antibodies; thus, they are commonly referred as SUMO2/3. In contrast, SUMO1 is distinct from SUMO2 and SUMO3, sharing only 50% amino acid homology with them.

SUMO conjugation, which is also referred to as SUMOylation has been established as a distinct protein post-translational modification pathway. Studies indicate the role of SUMOylation in cancer development and progression. See, Beeler, J. S., and Dejean, A., SUMO and robustness of cancer, *Nature Review Cancer* 17, 184-197 (2017).

We have investigated the mechanisms of SUMOylation in the development and progression of human cancers such as glioblastoma. It was found that SUMO1 conjugation is overactive in glioblastoma and drives the cancer growth through SUMO1 conjugation of the substrate protein CDK6 (cyclin-dependent kinase 6), CDK6 is a known cell cycle-driven kinase in cancer formation and growth. It was found that CDK6 is a substrate of both SUMO1 and ubiquitin (UB) and SUMO1-CDK6 conjugation inhibits CDK6 protein ubiquitination and UB-mediated degradation through the 26S proteasome and thereby stabilizes CDK6 protein and kinase activity that drives the cell cycle and cancer progression. See, Bellail, A. C., Olson, J. J., and Hao, C., SUMO1 modification stabilizes CDK6 protein and drives the cell cycle and glioblastoma progression, *Nature Communications* 5:4234 (2014).

Our studies have concluded that inhibition of SUMO1 conjugation can provide a therapeutic benefit against cancer. To target SUMO1 conjugation in cancer, we developed the cancer cell-based SUMO1 assays for drug screening and identified the compounds of the present invention that selectively induce the ubiquitination and degradation of SUMO1 but not SUMO2/3 protein in various types of cancer cells; therefore, the compounds act as SUMO1 protein degraders. Therapeutic induction of SUMO1 protein degradation and subsequent elimination of its conjugation by the present invention, therefore, offer the potential to develop a new class of anticancer drugs as described herein.

It is apparent from the foregoing that there is an ongoing need for developing safe and effective compounds as new therapeutic agents. It has surprisingly been found in the present invention that a family of benzothiazolyl urea or thiourea compounds are useful for SUMO1 protein degradation and represent a new family of compounds for treating certain types of cancers.

SUMMARY OF THE INVENTION

The present invention relates to the field of anti-cancer compounds. More particularly, the invention relates to a family of benzothiazolyl urea or thiourea compound useful as such therapeutic agents. The present invention also relates to methods for treating cancers using these compounds.

BRIEF DESCRIPTION OF THE DRAWINGS

FIG. 2A illustrates how the glioblastoma LN229 cell line was treated with each of compounds of the National Cancer Institute (NCI) Diversity Set IV library and analyzed by western blot assays using SUMO1, SUMO2/3, UB and β-actin antibodies. This cell-based screen identified compound 1 (CPD1) that selectively inhibits the conjugation of SUMO1 but not SUMO2/3 or UB.

FIG. 2B shows data where LN229 cells were treated with a series of dilutions of CPD1 for 3 days and examined by cell viability assay for cell growth inhibition (points: means±SD; n=6) with the $IC_{50}$ value indicated.

FIG. 2C shows data where LN229 cells were treated with CPD1 at the indicated doses and analyzed by western blotting for detection of the conjugated and free form of SUMO1 protein (left panels) and dot blotting for total levels of SUMO1 protein (right panels). The results show that CPD1 treatment reduces the conjugated, free form and total levels of SUMO1 proteins and indicate that CPD1 acts as a SUMO1 protein degrader.

FIG. 3A shows data where the compounds were analyzed by cell viability assays in treatment of LN229 cells, showing that compound 24 (CPD24) is much more potent in inhibition of the cancer cell growth.

FIG. 3B shows data where the LN229 cells were treated with each of the four compounds and analyzed by western and dot blot assays; the data show that the compound treatment reduces SUMO1 conjugation (left panel) and total protein levels of SUMO1 but not SUMO2/3 or UB (right panel).

FIG. 4A shows data where LN229 cells were treated with CPD1 or DMSO as a control, followed by the 26S proteasome inhibitor MG132 for the indicated times in hours and analyzed by western blot assays detecting conjugated and free SUMO1 protein (upper panel) and dot blot assay for the total levels of SUMO1 protein (lower panel). The data indicate that MG132 treatment prevents CPD1-induced degradation of SUMO1 protein, indicating that CPD1 induces SUMO1 degradation through the 26S proteasome.

FIG. 4B shows data where the non-conjugated form of Flag-tagged SUMO1 (Flag-SUMO1-GV) and the wild type (WT) HA-tagged UB (HA-UB-WT) were co-transfected in LN229 cells. The cells were treated with CPD1 (left panels) or CPD24 (right panels), Flag-SUMO1 was isolated through immunoprecipitation using Flag antibodies and tested by western blotting; the data show that the compound treatment results in the poly-ubiquitination of SUMO1 protein.

FIG. 4C shows data where the half-life of the SUMO1 protein was analyzed in LN229 cells under the treatment of CPD1, showing that the compound treatment reduces the half-life of SUMO1 protein from 11 hours to 1.5 hour.

FIG. 5A provides Western blot analyses of the normal epithelial lung Nuli-1 (left panel), colon IEC6 (middle panel) and breast MCF10A (right panel), together with matched cancer cell lines, demonstrate the markedly elevated levels of SUMO1 conjugation in cancer cells but not all normal cells. SUMO2/3 conjugation is observed in the normal lung but not colon and breast epithelial cells.

FIG. 5B provides Western blot (left panel) and dot blot analysis (right panel) of normal lung epithelial Nuli-1 and lung cancer cells treated or untreated with CPD24 show that CPD24 treatment reduces SUMO1 conjugation and total levels of SUMO1 protein in the cancer but not normal cells.

FIG. 5C shows the cell growth analysis of the National Cancer Institute-60 panel cancer lines shows that CPD1 treatment significantly inhibits the growth of breast, colon, lung, kidney, ovarian, prostate, skin (melanocytic) and blood (leukemic) cancers FIG. 5D shows the $IC_{50}$ values of cell viability assay show that the lead compound CDP1 is more potent than the hit compound CPD24 in inhibition of the growth of twenty-five lung, colon, breast and brain cancer cell lines.

FIG. 6A shows subcutaneous xenografts of colon HCT116 (top left graph) and lung A549 cancer cell lines (top right graph) which were treated with CPD1 or CPD24 and the data show that the treatment significantly suppressed xenograft progression (top right graph) but had no effect on the body weights of mice (bottom right graph).

FIG. 6B shows data for NOD/SCID mice bearing intracranial brain xenografts of glioblastoma LN229 cell line were treated with CPD1. Kaplan Meier survival analysis shows that the treatment increases the survival of intracranial xenograft mice, Statistical analysis was performed with log rank (Mantel-Cox) test.

FIG. 6C shows human derived xenografts (PDXs) of colon cancer (L1206F) and lung cancer (L1102F) which were treated with compounds CPD1 and CPD24. The left two graphs show data for compounds CPD1 and the middle two graphs show data for CPD24 treatment of colon cancer PDX (L1206F). The top panels of the left and middle graphs show that the CPD1 and CPD24 treatment significantly inhibits the tumor growth of the colon cancer PDXs as indicated by the tumor sizes; and the lower panels of the left and middle graphs show that the compound treatment had no effects on the body weight of mice. The right two graphs show data for compound CPD1 and CPD24 treatment of lung cancer PDX (L1102F). The top panel shows that the CPD1 and CPD24 treatment markedly inhibits the PDX growth with CPD24 more potent (in the lower doses of 25 mg/kg and 50 mg/kg that the dose of CPD1 at 100 mg/kg); and the lower panel shows no effects of the treatment on mouse body weight. These data indicate that the compound treatment significantly suppressed PDX progression of colon and lung cancer. The significance of P<0.01, and *P<0.001 was statistically analyzed.

DETAILED DESCRIPTION OF THE INVENTION

Figure 1:
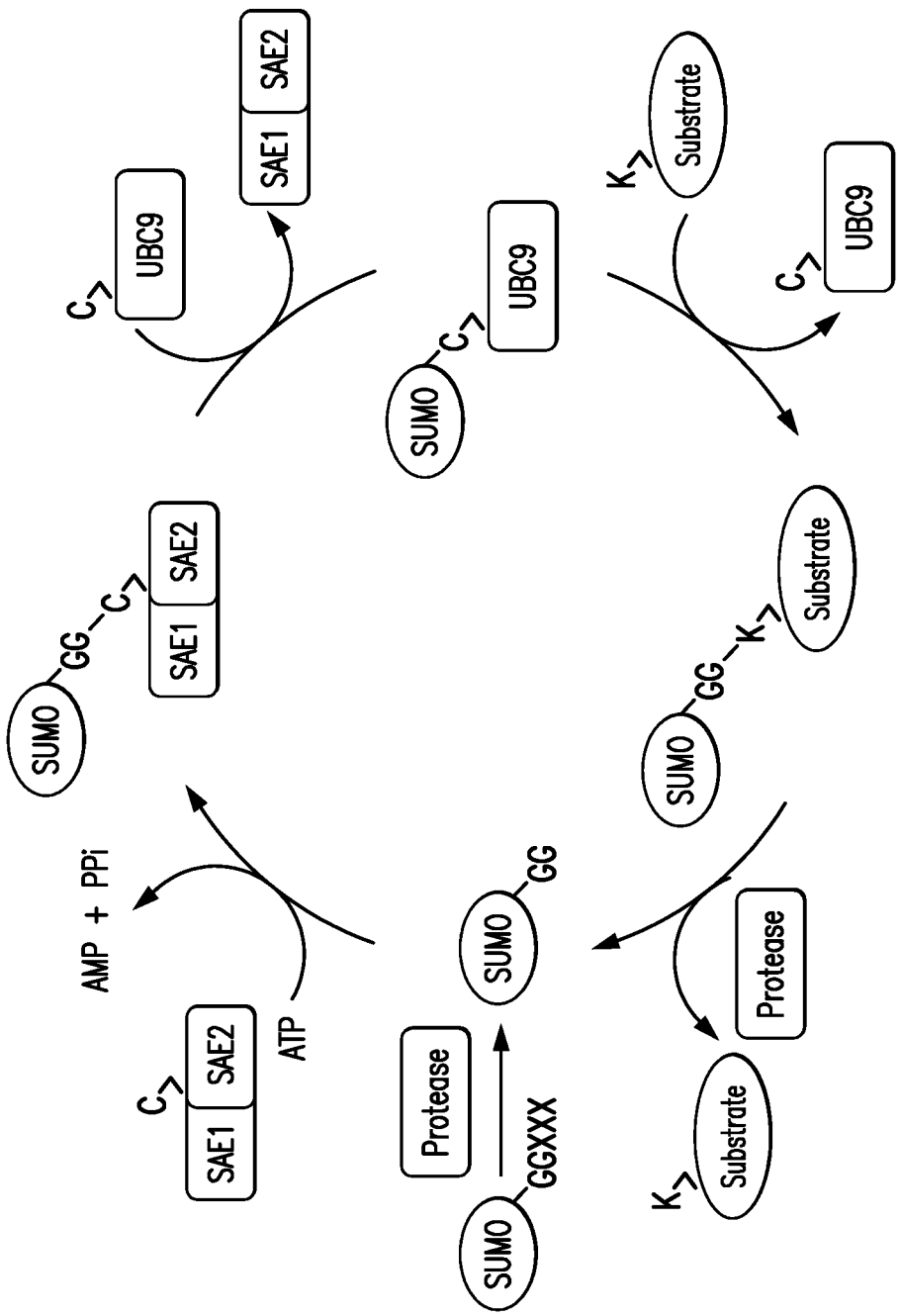
FIG. 1 shows a schematic representation of enzymatic SUMOylation reactions. The SUMO-GGXXX precursor is processed to the mature conjugated form SUMO-GG by SUMO proteases. The SAE1/2 dimmer (SUMO-activating enzyme-1/2, also known as enzyme 1, E1) carries a catalytic cysteine (C) that links and transfers SUMO-GG to the catalytic C on the E2 enzyme known as UB/SUMO-conjugation enzyme-9 (UBC9). SUMO-GG is transferred to the lysine (K) residue of a substrate protein and removed by a protease for another SUMOylation circle.

The present invention relates to a compound having the chemical Formula I

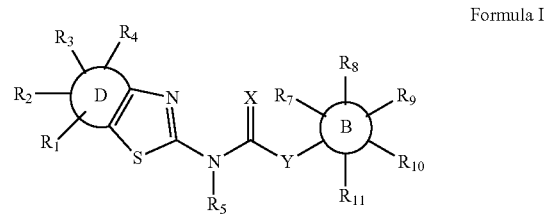

Formula I or a pharmaceutically acceptable salt or ester thereof, wherein
the substituent

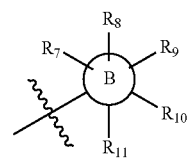

is selected from a 5- or 6-membered aromatic or heteroaromatic ring, a 8-, 9-, or 10-membered aromatic or heteroaromatic fused bicyclic ring, or a 5- to 10-membered saturated or partially unsaturated carbocyclic or heterocyclic ring, or fused bicycle ring, such rings having one or more substituents selected from $R_7$, $R_8$, $R_9$, $R_{10}$, and $R_{11}$;
the substituent

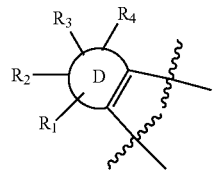

is a fused 5- or 6-membered aromatic or non-aromatic carbocyclic or hetereocyclic ring having one or more substituents selected from $R_1$, $R_2$, $R_3$, and $R_4$; wherein it should be appreciated that the D ring is fused to the benzothiazole ring;
Y is selected from —$CR_{15}R_{16}$— or —$NR_6$—;
each $R_1$, $R_2$, $R_3$, and $R_4$, when present, is independently selected from H, F, Cl, Br, I, OH, —$OR_{12}$, —O-aryl, —SH, —$SR_{12}$, —$SOR_{12}$, —$SO_2R_{12}$, —$NO_2$, —CN, —$NH_2$, —$NHR_{12}$, —$N(R_{12})_2$, —COOH, —$COOR_{12}$, —$C(O)NH_2$, —$C(O)NHR_{12}$, —$C(O)N(R_{12})_2$, —$OC(O)NH_2$, —$OC(O)NHR_{12}$, —$OC(O)N(R_{12})_2$, —$NHC(O)NH_2$, —$NHR_{12}C(O)NHR_{12}$, —$NHC(O)N(R_{12})_2$, —$NHCOOR_{12}$, —$NHR_{12}COOR_{12}$, —C(O)H, —$C(O)R_{12}$, $C_1$-$C_6$ alkyl or $C_3$-$C_6$ branched or cyclic alkyl, $C_2$-$C_6$ alkenyl or $C_3$-$C_6$ branched or cyclic alkenyl, $C_2$-$C_6$ alkynyl or $C_4$-$C_6$ branched or cyclic alkynyl, phenyl, 5- or 6-membered heteroaryl, and 8-, 9-, or 10-membered fused bicyclic aryl or heteroaryl, wherein each such $C_1$-$C_6$ alkyl or $C_3$-$C_6$ branched or cyclic alkyl, $C_2$-$C_6$ alkenyl or $C_3$-$C_6$ branched or cyclic alkenyl, $C_2$-$C_6$ alkynyl or $C_4$-$C_6$ branched or cyclic alkynyl, phenyl, 5- or 6-membered heteroaryl, and 8-, 9-, or 10-membered fused bicyclic aryl or heteroaryl, is optionally substituted with one or more $R_{13}$;
$R_5$, and $R_6$ are each independently selected from H or $C_1$-$C_6$ alkyl, alternatively $R_5$, and $R_6$ are taken together and selected from —$(CH_2)$— or —$(CH_2CH_2)$— to form a 5-membered or 6-membered ring with the atoms to which they are attached, and wherein each $R_5$ and $R_6$ are optionally substituted with one or more $R_{13}$;
each $R_7$, $R_8$, $R_9$, $R_{10}$, and $R_{11}$, when present, is independently selected from F, Cl, Br, I, —OH, —$OR_{12}$, —O-aryl, —SH, —$SR_{12}$, —$SOR_{12}$, —$SO_2R_{12}$, —$NO_2$, —CN, —$NH_2$, —$NHR_{12}$, —$N(R_{12})_2$, —COOH, —$COOR_{12}$, —$C(O)NH_2$, —$C(O)NHR_{12}$, —$C(O)N(R_{12})_2$, —$OC(O)NH_2$, —$OC(O)NHR_{12}$, —$OC(O)N(R_{12})_2$, —$NHC(O)NH_2$, —$NHR_{12}C(O)NHR_{12}$, —$NHC(O)N(R_{12})_2$, —$NHCOOR_{12}$, $NHR_{12}COOR_{12}$, —C(O)H, —$C(O)R_{12}$, $C_1$-$C_6$ alkyl or $C_3$-$C_6$ branched or cyclic alkyl, $C_2$-$C_6$ alkenyl or $C_3$-$C_6$ branched or cyclic alkenyl, $C_2$-$C_6$ alkynyl or $C_4$-$C_6$ branched or cyclic alkynyl, phenyl, 5- or 6-membered heterocycle, 5- or 6-membered heteroaryl, and 8-, 9-, or 10-membered fused bicyclic aryl or heteroaryl, wherein each such $C_1$-$C_6$ alkyl or $C_3$-$C_6$ branched or cyclic alkyl, $C_2$-$C_6$ alkenyl or $C_3$-$C_6$ branched or cyclic alkenyl, $C_2$-$C_6$ alkynyl or $C_4$-$C_6$ branched or cyclic alkynyl, phenyl, 5- or 6-membered heterocycle, 5- or 6-membered heteroaryl, and 8-, 9-, or 10-membered fused bicyclic aryl or heteroaryl, is optionally substituted with one or more $R_{13}$; alternatively two of $R_7$, $R_8$, $R_9$, $R_{10}$, and when present are selected from —$NR_{12}C(O)nR_{12}$— to form an attached 5-membered ring substituent;
each $R_{12}$ is independently selected from H or $C_1$-$C_6$ alkyl and is optionally substituted with one or more $R_{13}$, alternatively when two $R_{12}$ groups are on the same atom they can be joined together to form a 5- or 6-membered ring optionally containing —O— or —NH—;
each $R_{13}$ is independently selected from F, Cl, Br, I, —OH, —$OR_{14}$, —SH, —$SR_{14}$, —$NO_2$, —CN, —$NH_2$, —$NHR_{14}$, —$N(R_{14})_2$, —COOH, —$COOR_{14}$, —$C(O)NH_2$, —$C(O)NHR_{14}$, —$C(O)N(R_{14})_2$, —C(O)H, —$C(O)R_{14}$, $C_1$-$C_6$ alkyl or $C_3$-$C_6$ branched or cyclic alkyl, $C_2$-$C_6$ alkenyl or $C_3$-$C_6$ branched or cyclic alkenyl, $C_2$-$C_6$ alkynyl or $C_4$-$C_6$ branched or cyclic alkynyl, phenyl, 5- or 6-membered heteroaryl, and 8-, 9-, or 10-membered fused bicyclic aryl or heteroaryl;
each $R_{14}$ is independently selected from $C_1$-$C_6$ alkyl; and
each $R_{15}$ and $R_{16}$ when present are selected from $C_1$-$C_6$ alkyl or taken together with the atom to which they are attached to form a 3- to 6-membered ring.

In another aspect, the present invention relates to a compound of Formula II

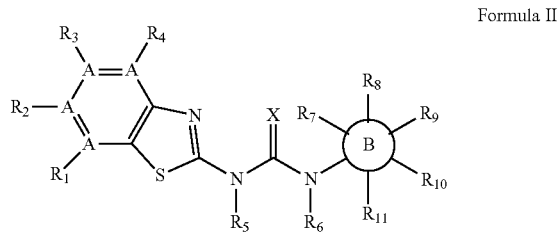

Formula II or a pharmaceutically acceptable salt or ester thereof, wherein
each A is independently selected from C or N, wherein when A is selected from N the indicated substituent $R_1$, $R_2$, $R_3$, or $R_4$ on that N is absent, and wherein no more than two A are simultaneously N;
the substituent

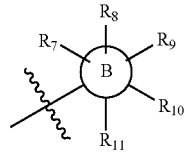

is selected from a 5- or 6-membered aromatic or heteroaromatic ring, a 8-, 9-, or 10-membered aromatic or heteroaromatic fused bicyclic ring, or a 5- to 10-membered saturated or partially unsaturated carbocyclic or heterocyclic ring or fused bicycle ring, such rings having one or more substituents selected from $R_7$, $R_8$, $R_9$, $R_{10}$, and $R_{11}$;
each $R_1$, $R_2$, $R_3$, and $R_4$, when present, is independently selected from H, F, Cl, Br, I, —OH, —$OR_{12}$, —O-aryl, —SH, —$SR_{12}$, —$SOR_2$, —$SO_2R_{12}$, —$NO_2$, —CN, —$NH_2$, —$NHR_{12}$, —$N(R_{12})_2$, —COOH, —$COOR_{12}$, —$C(O)NH_2$, —$C(O)NHR_{12}$, —$C(O)N(R_{12})_2$, —$OC(O)NH_2$, —$OC(O)NHR_{12}$, —$OC(O)N(R_{12})_2$, —$NHC(O)NH_2$, —$NHR_{12}C(O)NHR_{12}$, —$NHC(O)N(R_{12})_2$, —$NHCOOR_{12}$, $NHR_{12}COOR_{12}$, —C(O)H, —$C(O)R_{12}$, $C_1$-$C_6$ alkyl or $C_3$-$C_6$ branched or cyclic alkyl, $C_2$-$C_6$ alkenyl or $C_3$-$C_6$ branched or cyclic alkenyl, $C_2$-$C_6$ alkynyl or $C_4$-$C_6$ branched or cyclic alkynyl, phenyl, 5- or 6-membered heteroaryl, and 8-, 9-, or 10-membered fused bicyclic aryl or heteroaryl, wherein each such $C_1$-$C_6$ alkyl or $C_3$-$C_6$ branched or cyclic alkyl, $C_2$-$C_6$ alkenyl or $C_3$-$C_6$ branched or cyclic alkenyl, $C_2$-$C_6$ alkynyl or $C_4$-$C_6$ branched or cyclic alkynyl, phenyl, 5- or 6-membered heteroaryl, and 8-, 9-, or 10-membered fused bicyclic aryl or heteroaryl, is optionally substituted with one or more $R_{13}$;

$R_5$, and $R_6$ are each independently selected from H or $C_1$-$C_6$ alkyl, alternatively $R_5$, and $R_6$ are taken together and selected from —$(CH_2)$— or —$(CH_2CH_2)$— to form a 5-membered or 6-membered ring with the atoms to which they are attached, and wherein each $R_5$ and $R_6$ are optionally substituted with one or more $R_{13}$;

each $R_7$, $R_8$, $R_9$, $R_{10}$, and $R_{11}$, when present, is independently selected from F, Cl, Br, I, —OH, —$OR_{12}$, —O-aryl, —SH, —$SR_{12}$, —$SOR_{12}$, —$SO_2R_{12}$, —$NO_2$, —CN, —$NH_2$, —$NHR_{12}$, —$N(R_{12})_2$, —COOH, —$COOR_{12}$, —$C(O)NH_2$, —$C(O)NHR_{12}$, —$C(O)N(R_{12})_2$, —$OC(O)NH_2$, —$OC(O)NHR_{12}$, —$OC(O)N(R_{12})_2$, —$NHC(O)NH_2$, —$NHR_{12}C(O)NHR_{12}$, —$NHC(O)N(R_{12})_2$, —$NHCOOR_{12}$, $NHR_{12}COOR_{12}$, —C(O)H, —$C(O)R_{12}$, $C_1$-$C_6$ alkyl or $C_3$-$C_6$ branched or cyclic alkyl, $C_2$-$C_6$ alkenyl or $C_3$-$C_6$ branched or cyclic alkenyl, $C_2$-$C_6$ alkynyl or $C_4$-$C_6$ branched or cyclic alkynyl, phenyl, 5- or 6-membered heterocycle, 5- or 6-membered heteroaryl, and 8-, 9-, or 10-membered fused bicyclic aryl or heteroaryl, wherein each such $C_1$-$C_6$ alkyl or $C_3$-$C_6$ branched or cyclic alkyl, $C_2$-$C_6$ alkenyl or $C_3$-$C_6$ branched or cyclic alkenyl, $C_2$-$C_6$ alkynyl or $C_4$-$C_6$ branched or cyclic alkynyl, phenyl, 5- or 6-membered heterocycle, 5- or 6-membered heteroaryl, and 8-, 9-, or 10-membered fused bicyclic aryl or heteroaryl, is optionally substituted with one or more $R_{13}$; alternatively two of $R_7$, $R_8$, $R_9$, $R_{10}$, and $R_{11}$, when present are selected from —$NR_{12}C(O)nR_{12}$— to form an attached 5-membered ring substituent;

each $R_{12}$ is independently selected from H or $C_1$-$C_6$ alkyl and is optionally substituted with one or more $R_{13}$, alternatively when two $R_{12}$ groups are on the same atom they can be joined together to form a 5- or 6-membered ring optionally containing —O— or —NH—;

each $R_{13}$ is independently selected from F, Cl, Br, I, —OH, —$OR_{14}$, —SH, —$SR_{14}$, —$NO_2$, —CN, —$NH_2$, —$NHR_{14}$, —$N(R_{14})_2$, —COOH, —$COOR_{14}$, —$C(O)NH_2$, —$C(O)NHR_{14}$, —$C(O)N(R_{14})_2$, —C(O)H, —$C(O)R_{14}$, $C_1$-$C_6$ alkyl or $C_3$-$C_6$ branched or cyclic alkyl, $C_2$-$C_6$ alkenyl or $C_3$-$C_6$ branched or cyclic alkenyl, $C_2$-$C_6$ alkynyl or $C_4$-$C_6$ branched or cyclic alkynyl, phenyl, 5- or 6-membered heteroaryl, and 8-, 9-, or 10-membered fused bicyclic aryl or heteroaryl; and each $R_{14}$ is independently selected from $C_1$-$C_6$ alkyl.

In another aspect, the present invention relates to a compound of Formula I or II wherein the substituent

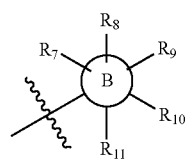

is a 5- or 6-membered aromatic or heteroaromatic ring, having one or more substituents selected from $R_7$, $R_8$, $R_9$, $R_{10}$, and $R_{11}$.

In another aspect, the present invention relates to a compound having the chemical Formula III

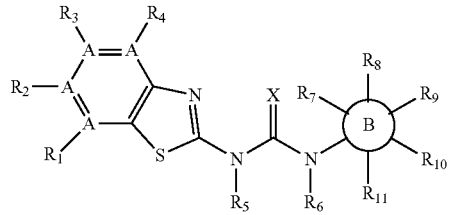

Formula II or a pharmaceutically acceptable salt or ester thereof, wherein each A is independently selected from C or N, wherein when A is selected from N the indicated substituent $R_1$, $R_2$, $R_3$, or $R_4$ on that N is absent, and wherein no more than two A are simultaneously N;

the substituent

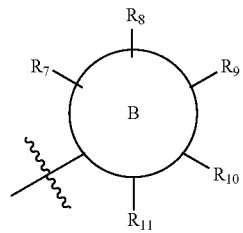

is selected from a 5- or 6-membered aromatic or heteroaromatic ring, a 8-, 9-, or 10-membered aromatic or heteroaromatic fused bicyclic ring, or a 5- to 10-membered saturated or partially unsaturated carbocyclic or heterocyclic ring or fused bicycle ring, such rings having one or more substituents selected from $R_7$, $R_8$, $R_9$, $R_{10}$, and $R_{11}$;

each $R_1$, $R_2$, $R_3$, and $R_4$, when present, is independently selected from H, F, Cl, Br, I, —OH, —$OR_{12}$, —O-aryl, —SH, —$SR_{12}$, —$SOR_{12}$, —$SO_2R_{12}$, —$NO_2$, —CN, —$NH_2$, —$NHR_{12}$, —$N(R_{12})_2$, —COOH, —$COOR_{12}$, —$C(O)NH_2$, —$C(O)NHR_{12}$, —$C(O)N(R_{12})_2$, —$OC(O)NH_2$, —$OC(O)NHR_{12}$, —$OC(O)N(R_{12})_2$, —$NHC(O)NH_2$, —$NHR_{12}C(O)NHR_{12}$, —$NHC(O)N(R_{12})_2$, —$NHCOOR_{12}$, —$NHR_{12}COOR_{12}$, —C(O)H, —$C(O)R_{12}$, $C_1$-$C_6$ alkyl or $C_3$-$C_6$ branched or cyclic alkyl, $C_2$-$C_6$ alkenyl or $C_3$-$C_6$ branched or cyclic alkenyl, $C_2$-$C_6$ alkynyl or $C_4$-$C_6$ branched or cyclic alkynyl, phenyl, 5- or 6-membered heteroaryl, and 8-, 9-, or 10-membered fused bicyclic aryl or heteroaryl, wherein each such $C_1$-$C_6$ alkyl or $C_3$-$C_6$ branched or cyclic alkyl, $C_2$-$C_6$ alkenyl or $C_3$-$C_6$ branched or cyclic alkenyl, $C_2$-$C_6$ alkynyl or $C_4$-$C_6$ branched or cyclic alkynyl, phenyl, 5- or 6-membered heteroaryl, and 8-, 9-, or 10-membered fused bicyclic aryl or heteroaryl, is optionally substituted with one or more $R_{13}$;

$R_5$, and $R_6$ are each independently selected from H or $C_1$-$C_6$ alkyl, alternatively $R_5$, and $R_6$ are taken together and selected from —$(CH_2)$— or —$(CH_2CH_2)$— to form a 5-membered or 6-membered ring with the atoms to which they are attached, and wherein each $R_5$ and $R_6$ are optionally substituted with one or more $R_{13}$;

each $R_7$, $R_8$, $R_9$, $R_{10}$, and $R_{11}$, when present, is independently selected from F, Cl, Br, I, —OH, —$OR_{12}$, —O-aryl, —SH, —$SR_{12}$, —$SOR_{12}$, —$SO_2R_{12}$, —$NO_2$, —CN, —$NH_2$, —$NHR_{12}$, —$N(R_{12})_2$, —COOH, —$COOR_{12}$, —$C(O)NH_2$, —$C(O)NHR_{12}$, —$C(O)N(R_{12})_2$, —$OC(O)NH_2$, —$OC(O)NHR_{12}$, —$OC(O)N(R_{12})_2$, —$NHC(O)NH_2$, —NHR$_{12}$C(O)NHR$_{12}$, —NHC(O)N(R$_{12}$)$_2$, —NHCOOR$_{12}$, —NHR$_{12}$COOR$_{12}$, —C(O)H, —C(O)R$_{12}$, C$_1$-C$_6$ alkyl or C$_3$-C$_6$ branched or cyclic alkyl, C$_2$-C$_6$ alkenyl or C$_3$-C$_6$ branched or cyclic alkenyl, C$_2$-C$_6$ alkynyl or C$_4$-C$_6$ branched or cyclic alkynyl, phenyl, 5- or 6-membered heterocycle, 5- or 6-membered heteroaryl, and 8-, 9-, or 10-membered fused bicyclic aryl or heteroaryl, wherein each such C$_1$-C$_6$ alkyl or C$_3$-C$_6$ branched or cyclic alkyl, C$_2$-C$_6$ alkenyl or C$_3$-C$_6$ branched or cyclic alkenyl, C$_2$-C$_6$ alkynyl or C$_4$-C$_6$ branched or cyclic alkynyl, phenyl, 5- or 6-membered heterocycle, 5- or 6-membered heteroaryl, and 8-, 9-, or 10-membered fused bicyclic aryl or heteroaryl, is optionally substituted with one or more R$_{13}$; alternatively two of R$_7$, R$_8$, R$_9$, R$_{10}$, and R$_{11}$, when present are selected from —NR$_{12}$C(O)nR$_{12}$— to form an attached 5-membered ring substituent;

each R$_{12}$ is independently selected from H or C$_1$-C$_6$ alkyl and is optionally substituted with one or more R$_{13}$, alternatively when two R$_{12}$ groups are on the same atom they can be joined together to form a 5- or 6-membered ring optionally containing —O— or —NH—;

each R$_{13}$ is independently selected from F, Cl, Br, I, —OH, —OR$_{14}$, —SH, —SR$_{14}$, —NO$_2$, —CN, —NH$_2$, —NHR$_{14}$, —N(R$_{14}$)$_2$, —COOH, —COOR$_{14}$, —C(O)NH$_2$, —C(O)NHR$_{14}$, —C(O)N(R$_{14}$)$_2$, —C(O)H, —C(O)R$_{14}$, C$_1$-C$_6$ alkyl or C$_3$-C$_6$ branched or cyclic alkyl, C$_2$-C$_6$ alkenyl or C$_3$-C$_6$ branched or cyclic alkenyl, C$_2$-C$_6$ alkynyl or C$_4$-C$_6$ branched or cyclic alkynyl, phenyl, 5- or 6-membered heteroaryl, and 8-, 9-, or 10-membered fused bicyclic aryl or heteroaryl; and each R$_{14}$ is independently selected from C$_1$-C$_6$ alkyl.

In another aspect, the present invention relates to a compound of Formula I, II, or III wherein X is O.

In another aspect, the present invention relates to a compound of Formula I, II, or III wherein R$_1$ and R$_4$ are both H.

In another aspect, the present invention relates to a compound of Formula I, II, or III wherein R$_5$ and R$_6$ are both H.

In another aspect, the present invention relates to a compound of Formula I, II, or III wherein at least one of R$_2$ and R$_3$ is selected from F, Cl, Br, I, —NO$_2$ or, —CN.

In another aspect, the present invention relates to a compound of Formula I, II, or III wherein at least one of R$_2$ and R$_3$ is selected from —NO$_2$ or —CN.

In another aspect, the present invention relates to a compound of Formula I, II, or III wherein at least one of R$_2$ and R$_3$ is selected from —CN.

In another aspect, the present invention relates to a compound of Formula I, II, or III wherein at least one of R$_2$ and R$_3$ is selected from —NO$_2$.

In another aspect, the present invention relates to a compound of Formula I, II, or III wherein R$_7$ and R$_{11}$ are H.

In another aspect, the present invention relates to a compound according to Formula I, II, or III, wherein alternatively one or more of each of R$_1$, R$_2$, R$_3$, R$_4$, R$_7$, R$_8$, R$_9$, R$_{10}$, and R$_{11}$, when present are selected from —(OCH$_2$CH$_2$)$_n$—O-aryl, —C(O)—(OCH$_2$CH$_2$)$_n$—O-aryl, —(OCH$_2$CH$_2$)$_n$—N(R$_{12}$)$_2$, —C(O)—(OCH$_2$CH$_2$)$_n$—N(R$_{12}$)$_2$, —(OCH$_2$CH$_2$)$_n$—N(R$_{12}$)C(O)R$_{12}$, —C(O)—(OCH$_2$CH$_2$)$_n$—N(R$_{12}$)C(O)R$_{12}$, and combinations thereof, wherein n is an integer from 1 to 10 and aryl is optionally substituted with one or more R$_{13}$.

In another aspect, the present invention relates to a compound having a chemical structure selected from the following Compounds 1 to 77 and 79 to 195, or combinations thereof, including pharmaceutically acceptable salts or esters thereof:

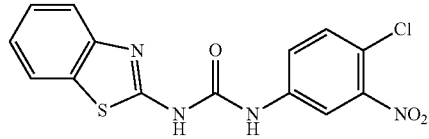

Compound 1

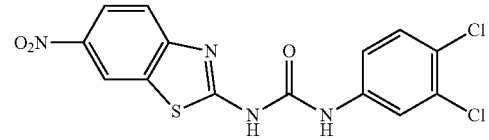

Compound 2

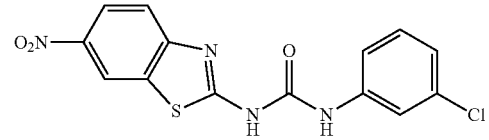

Compound 3

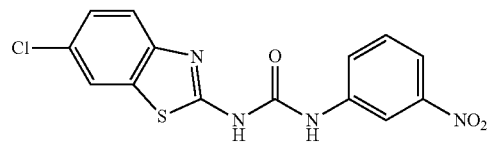

Compound 4

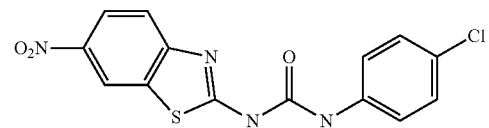

Compound 5

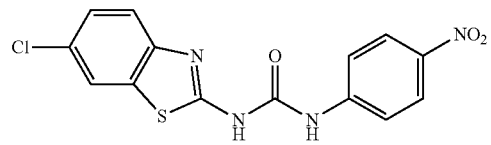

Compound 6

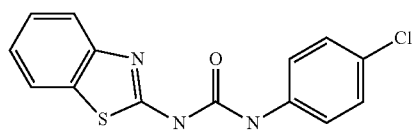

Compound 7

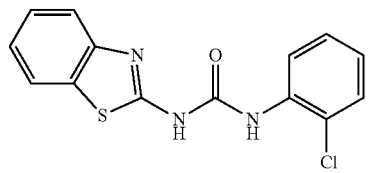

Compound 8

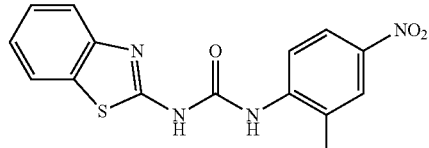

Compound 9

Compound 10
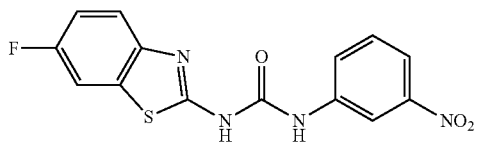
Compound 11
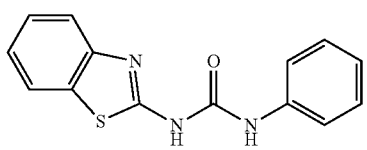
Compound 12
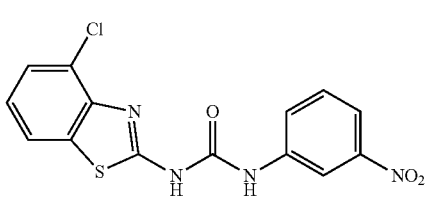
Compound 13
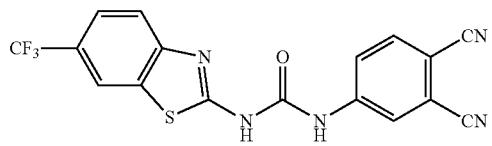
Compound 14
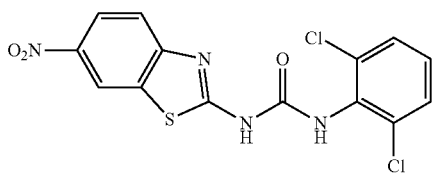
Compound 15
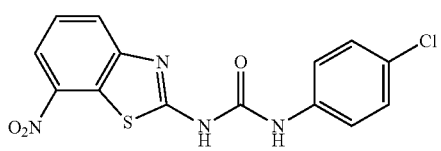
Compound 16
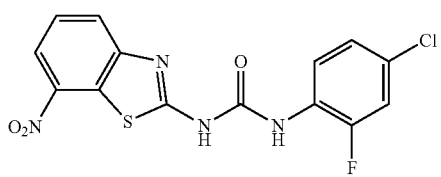
Compound 17
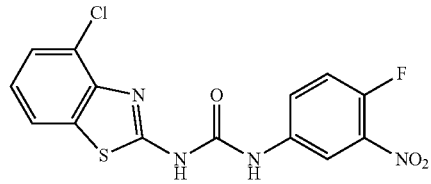
Compound 18
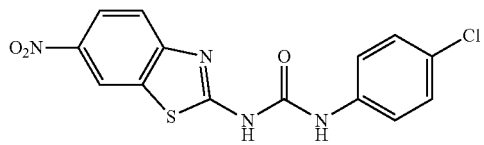
Compound 19
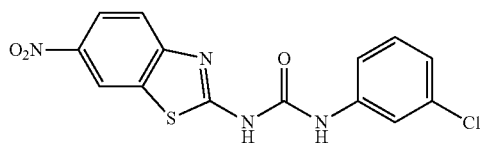
Compound 20
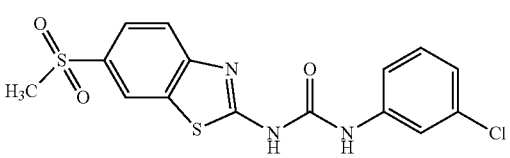
Compound 21
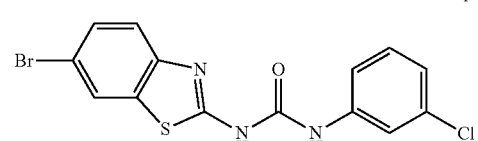
Compound 22
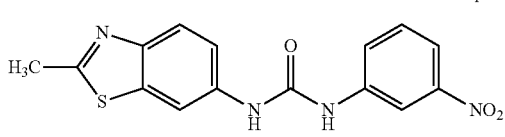
Compound 23
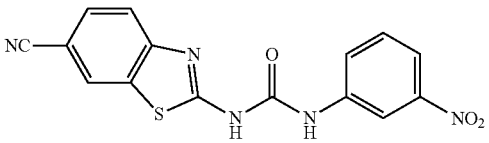
Compound 24
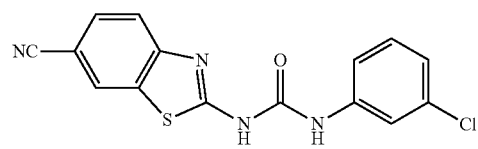
Compound 25
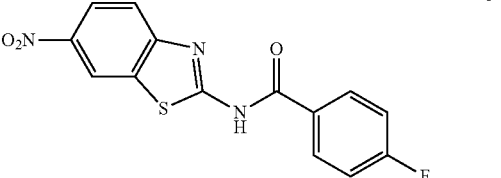
Compound 26
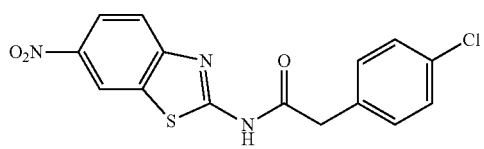

Compound 27
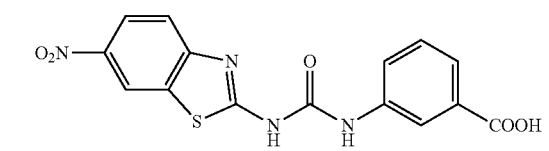
Compound 28
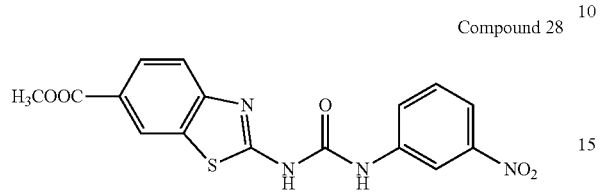
Compound 29
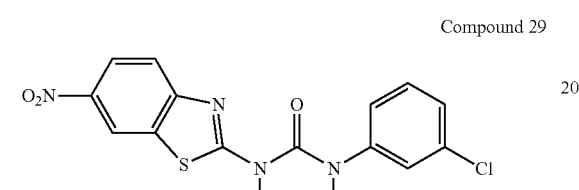
Compound 30
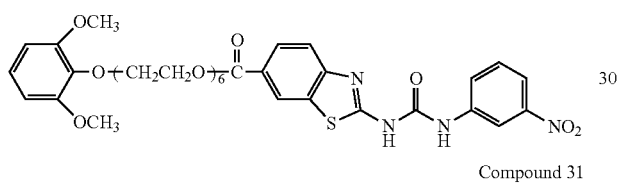
Compound 31
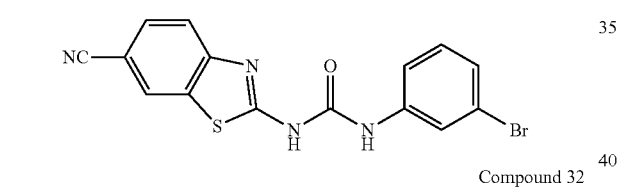
Compound 32
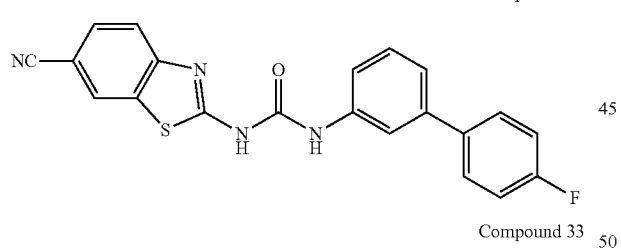
Compound 33
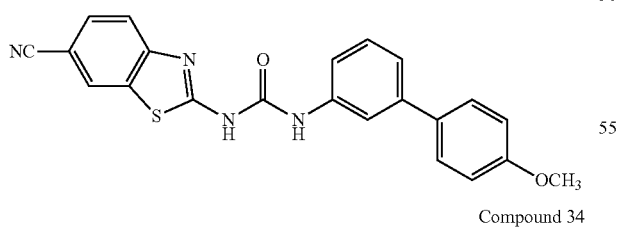
Compound 34
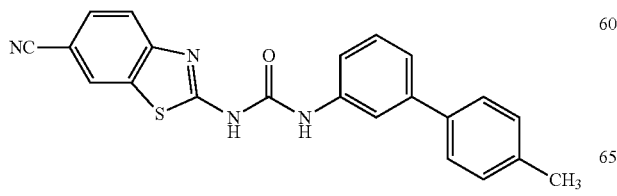
Compound 35
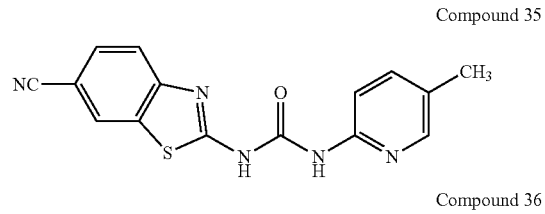
Compound 36
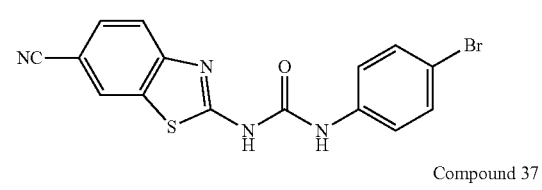
Compound 37
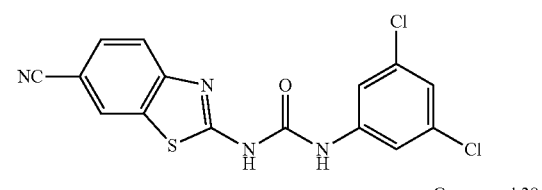
Compound 38
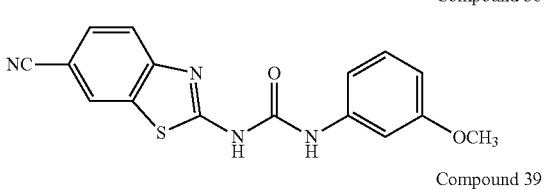
Compound 39
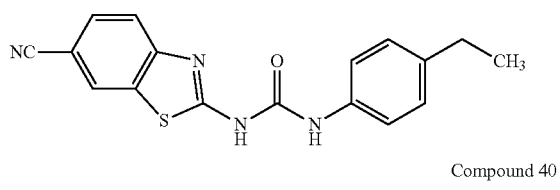
Compound 40
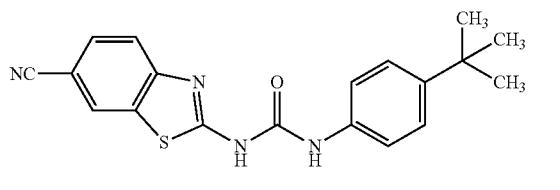
Compound 41
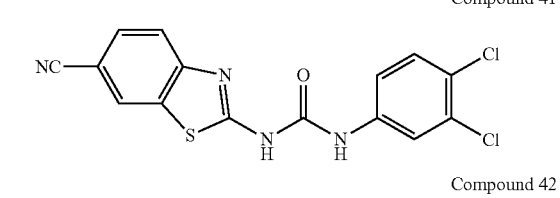
Compound 42
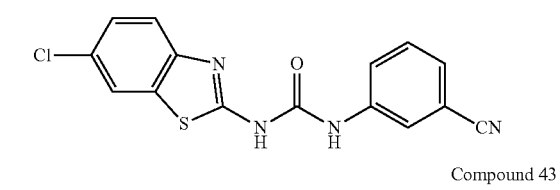
Compound 43
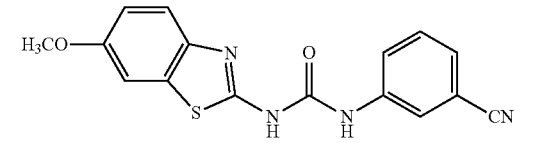

Compound 44
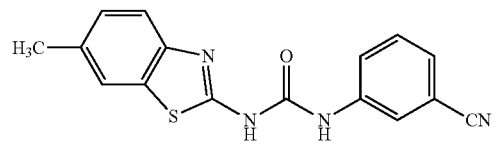
Compound 45
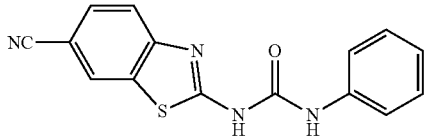
Compound 46
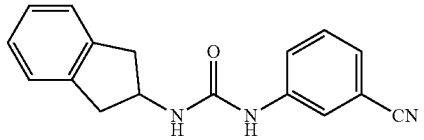
Compound 47
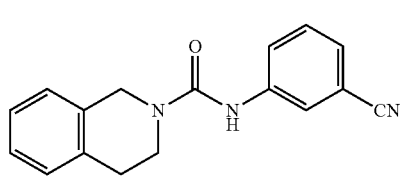
Compound 48
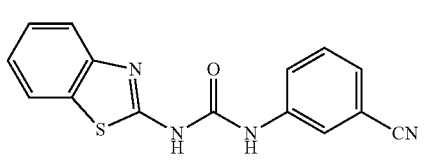
Compound 49
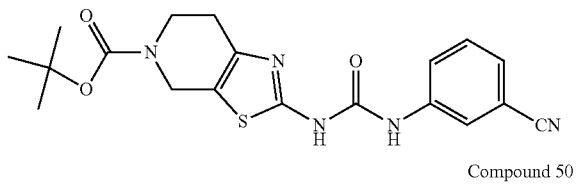
Compound 50
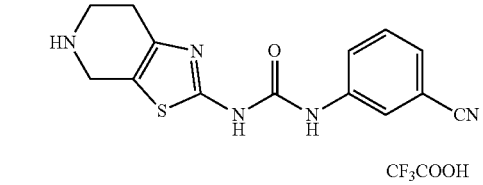
CF₃COOH
Compound 51
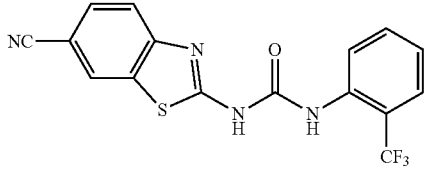
Compound 52
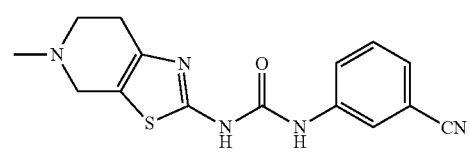
Compound 53
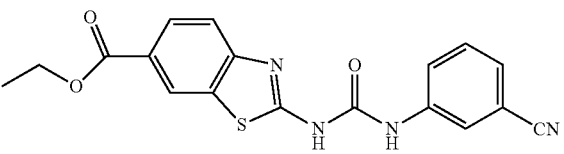
Compound 54
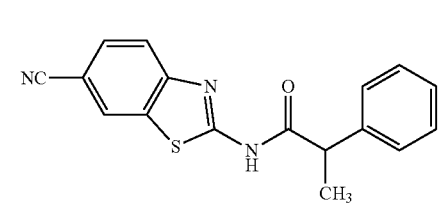
Compound 55
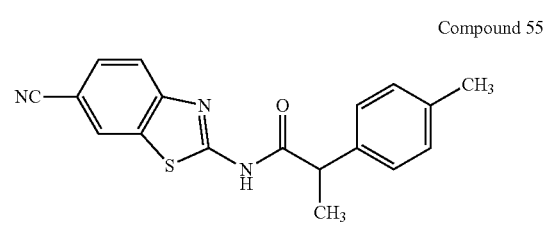
Compound 56
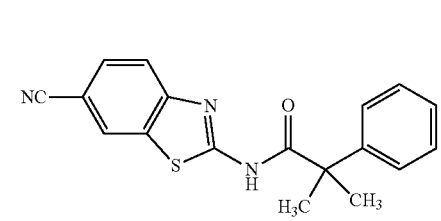
Compound 57
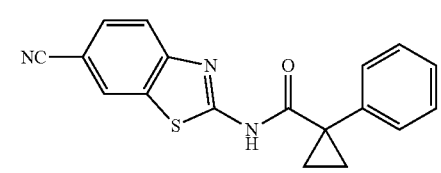
Compound 58
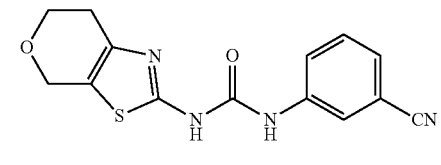
Compound 59
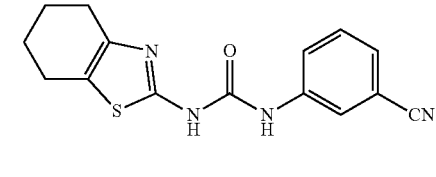
Compound 60
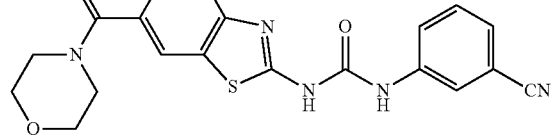

-continued
Compound 61
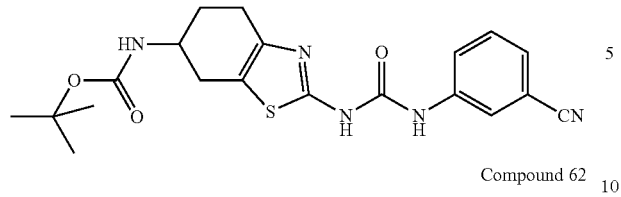
Compound 62
Compound 63
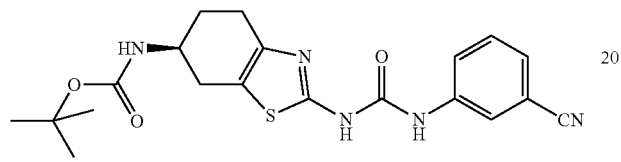
Compound 64
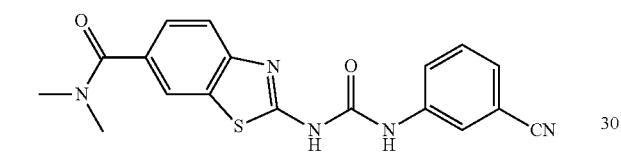
Compound 65
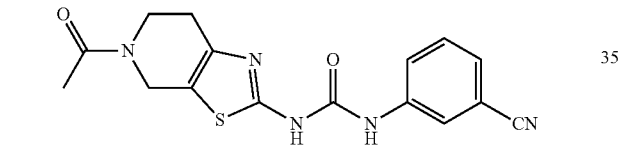
Compound 66
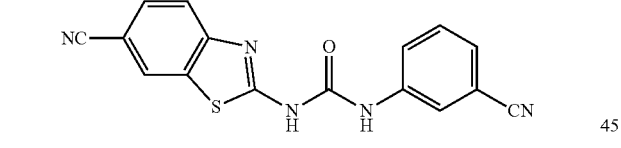
Compound 67
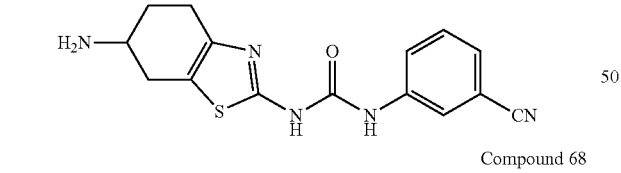
Compound 68
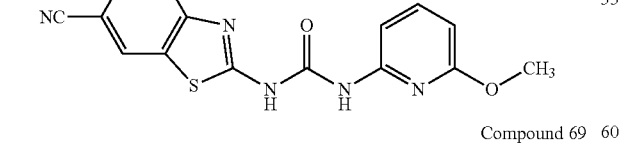
Compound 69
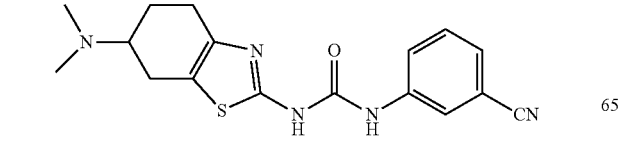
-continued
Compound 70
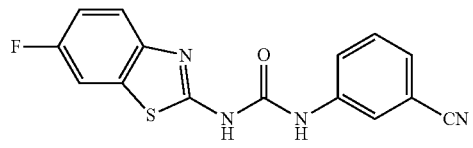
Compound 71
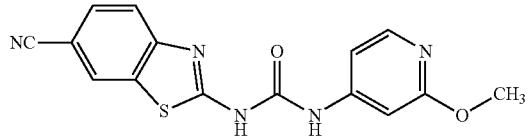
Compound 72
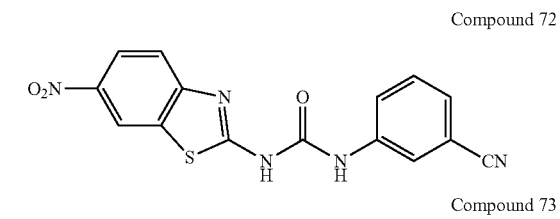
Compound 73
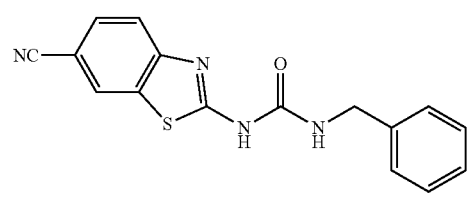
Compound 74
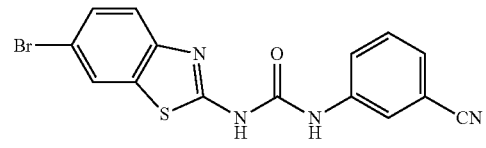
Compound 75
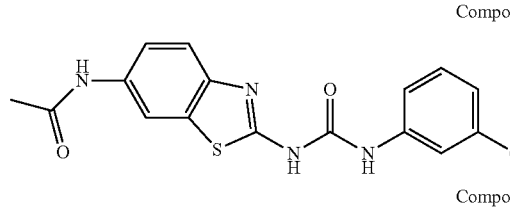
Compound 76
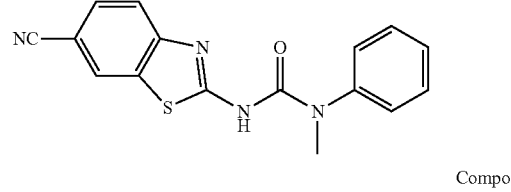
Compound 77
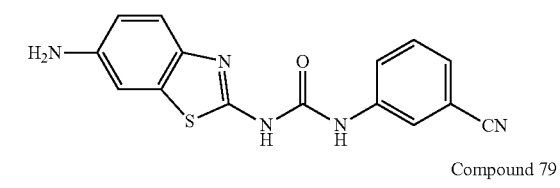
Compound 79
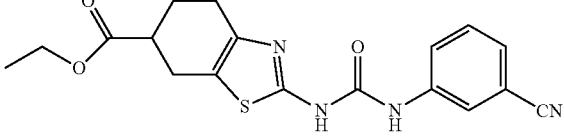

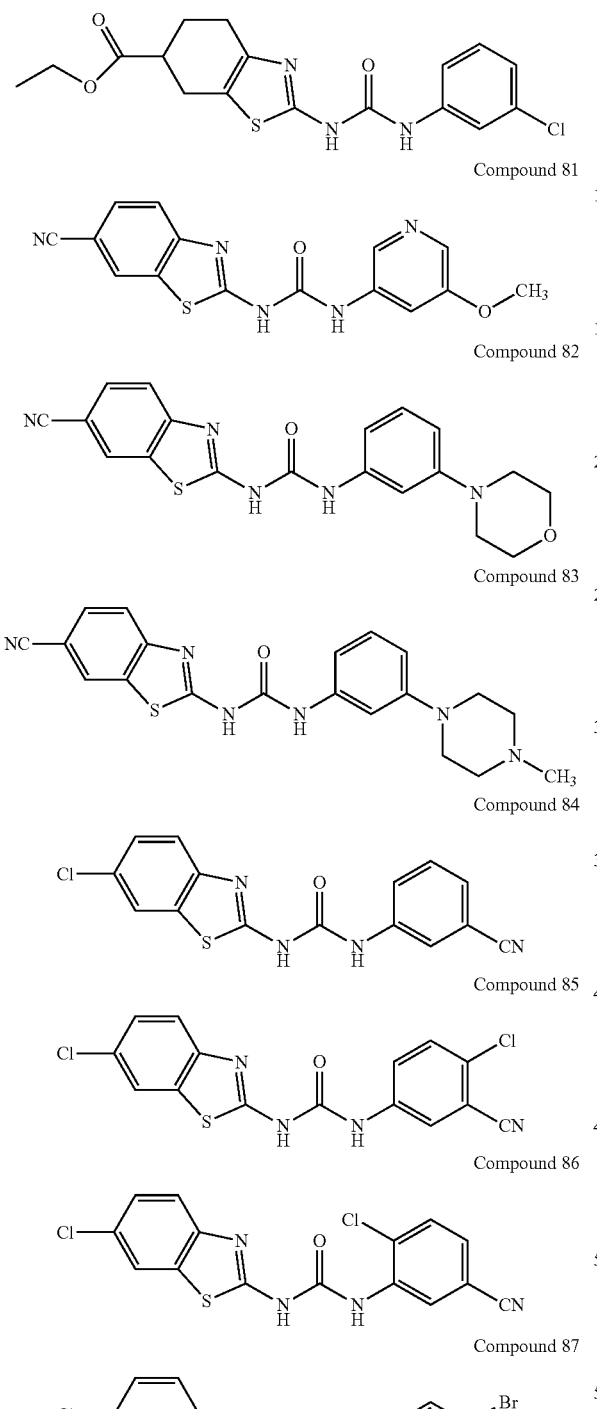
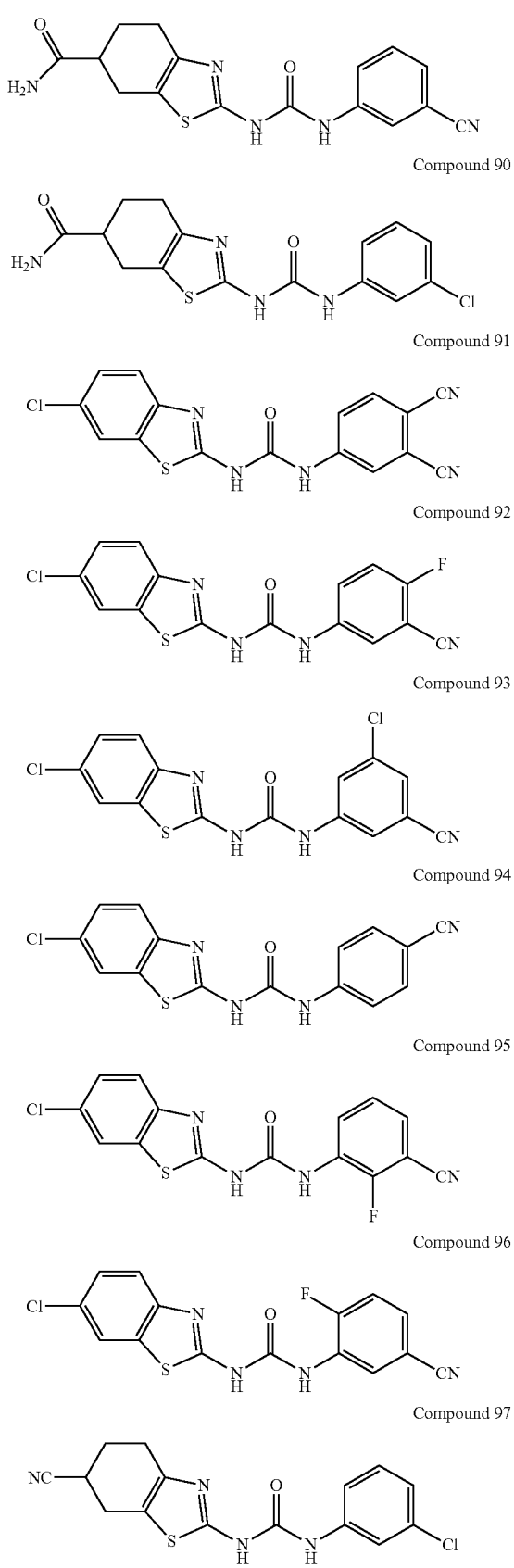

Compound 98
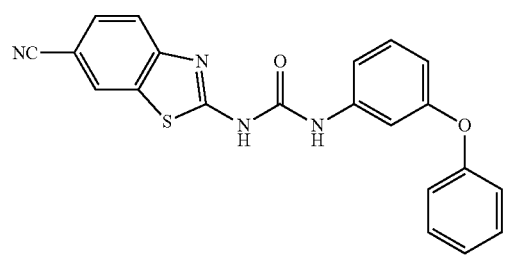
Compound 99
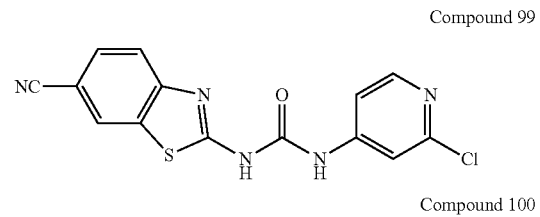
Compound 100
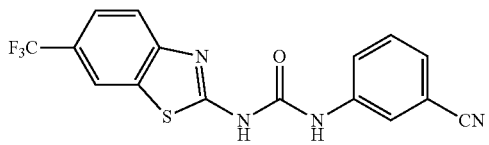
Compound 101
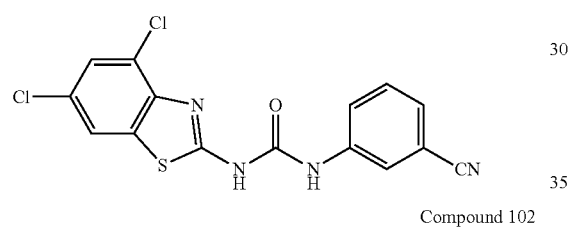
Compound 102
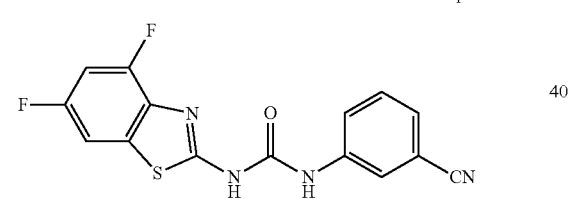
Compound 103
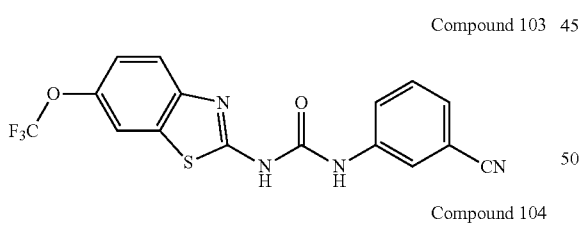
Compound 104
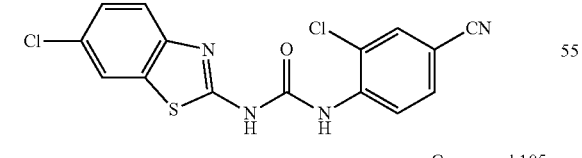
Compound 105
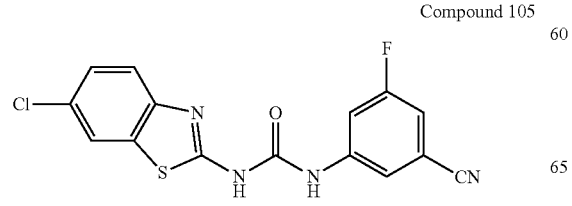
Compound 106
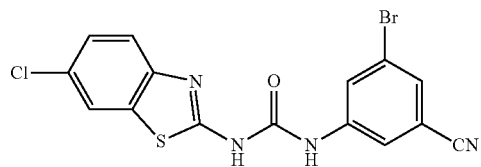
Compound 107
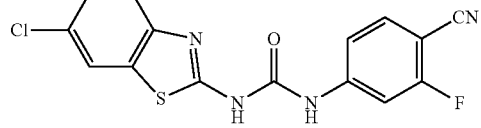
Compound 108
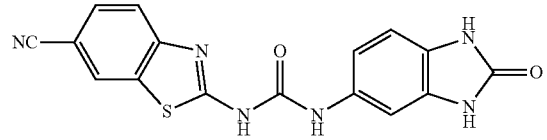
Compound 109
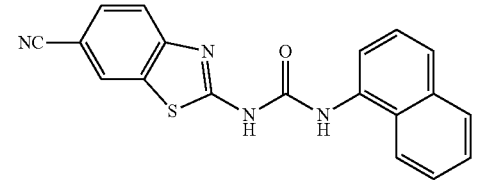
Compound 110
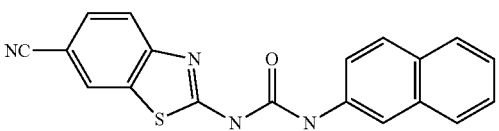
Compound 111
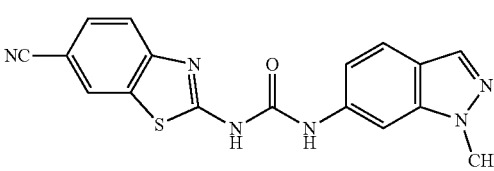
Compound 112
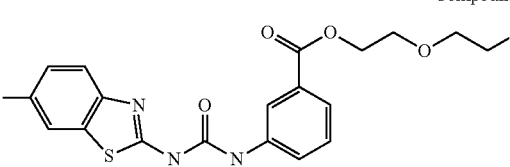
Compound 113
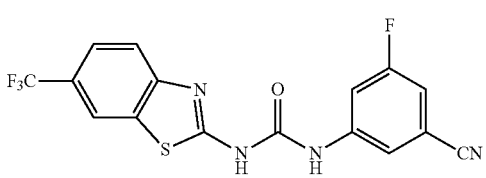

Compound 114
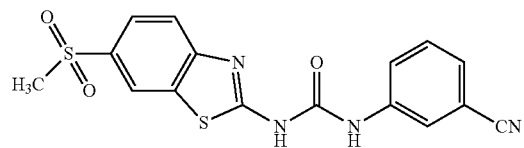
Compound 115
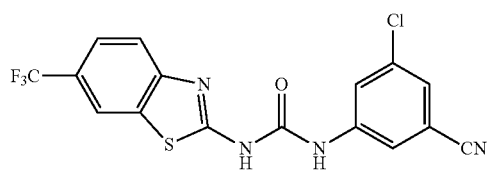
Compound 116
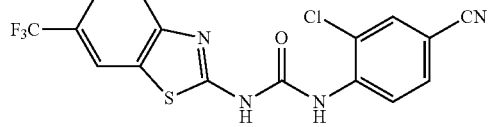
Compound 117
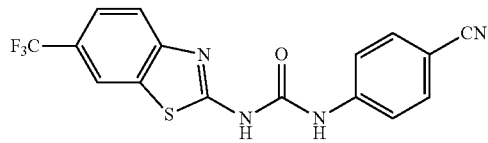
Compound 118
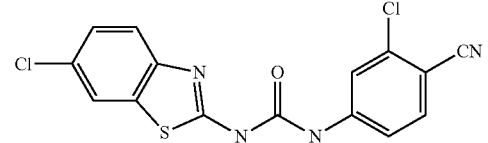
Compound 119
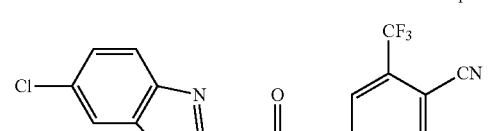
Compound 120
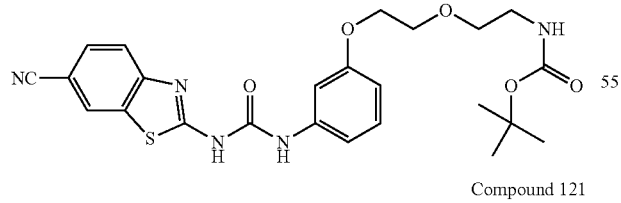
Compound 121
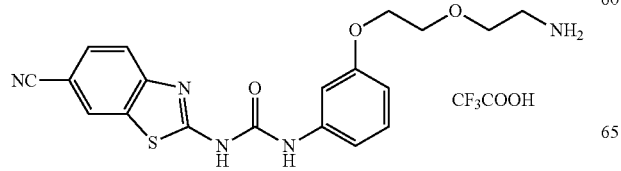
CF₃COOH
Compound 122
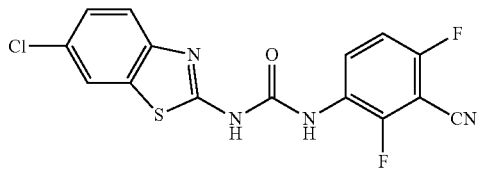
Compound 123
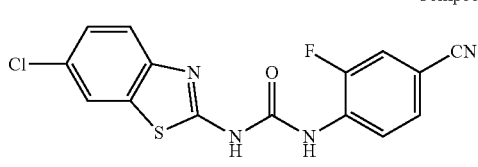
Compound 124
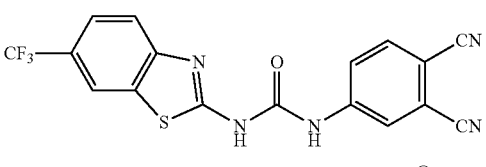
Compound 125
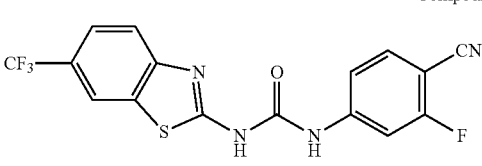
Compound 126
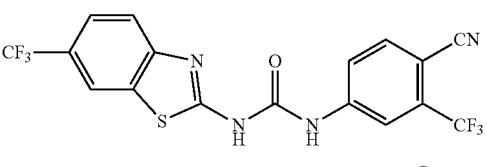
Compound 127
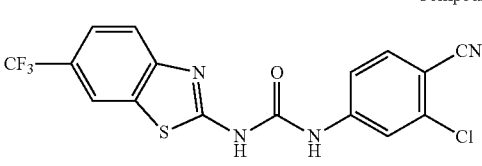
Compound 128
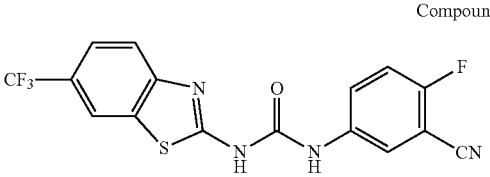
Compound 129
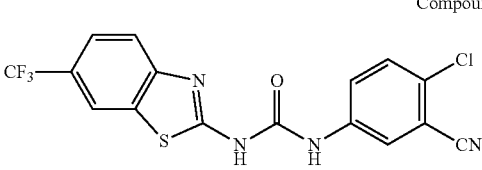
Compound 130
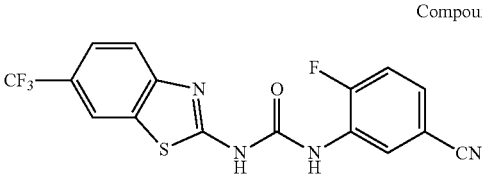

Compound 131
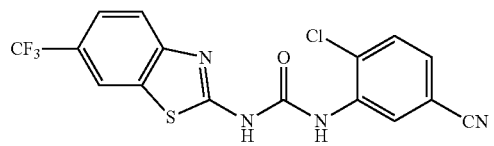
Compound 132
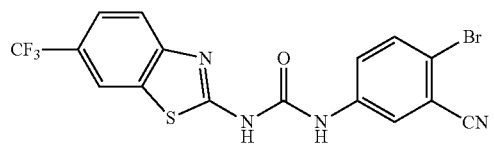
Compound 133
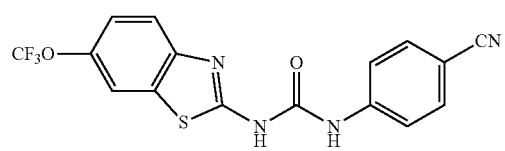
Compound 134
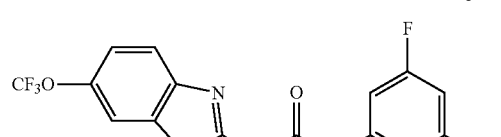
Compound 135
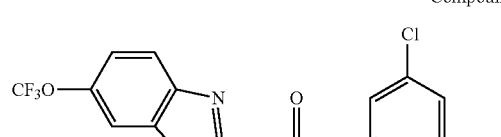
Compound 136
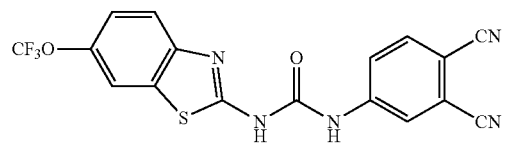
Compound 137
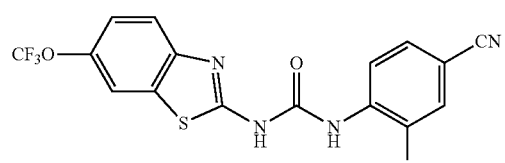
Compound 138
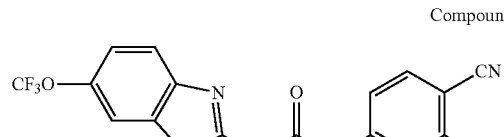
Compound 139
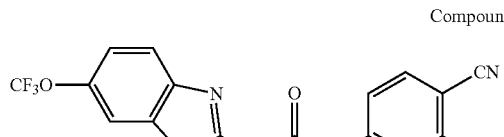
Compound 140
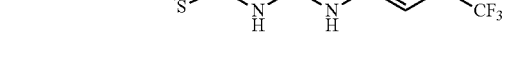
Compound 141
Compound 142
Compound 143
Compound 144
Compound 145
Compound 146
Compound 147

Compound 148
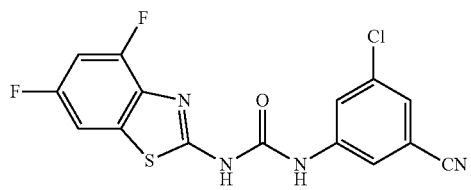
Compound 149
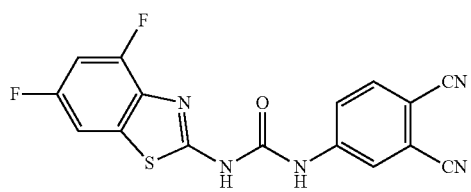
Compound 150
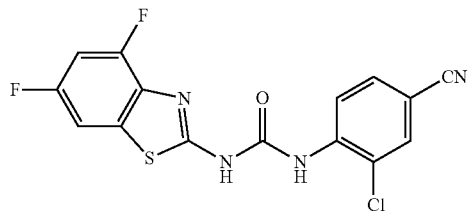
Compound 151
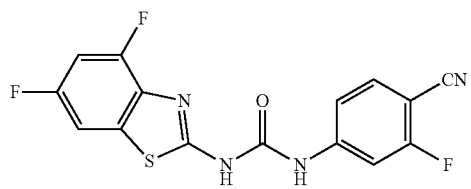
Compound 152
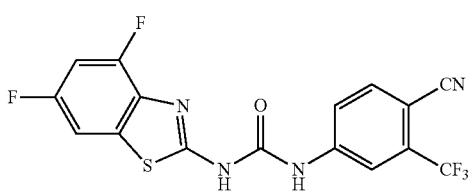
Compound 153
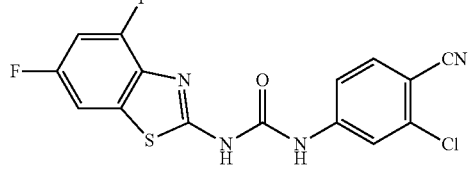
Compound 154
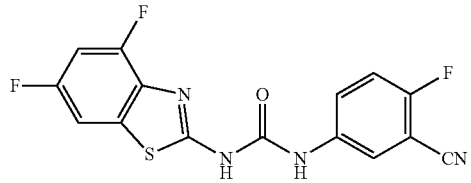
Compound 155
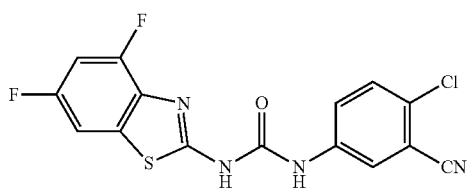
Compound 156
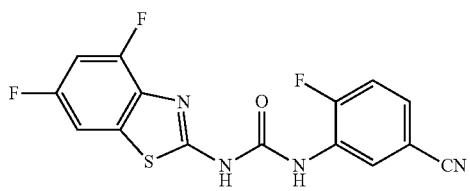
Compound 157
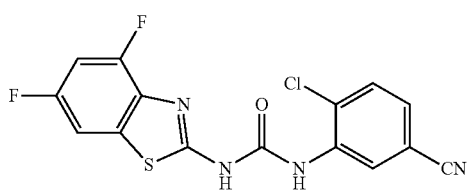
Compound 158
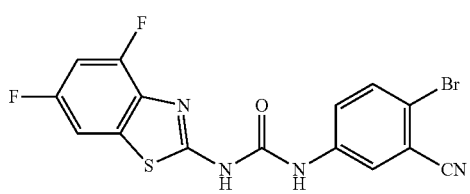
Compound 159
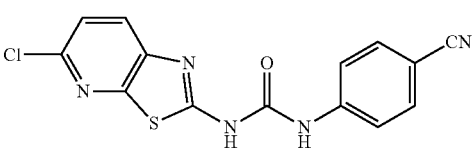
Compound 160
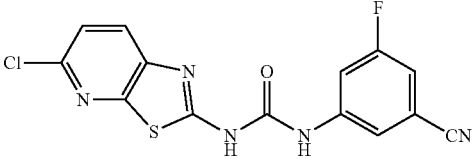
Compound 161
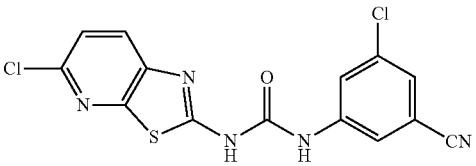
Compound 162
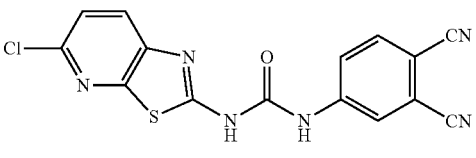

Compound 163
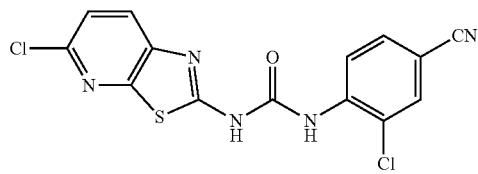
Compound 164
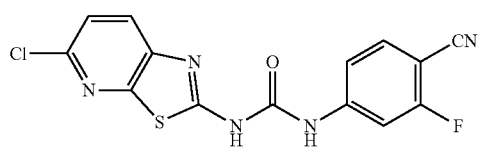
Compound 165
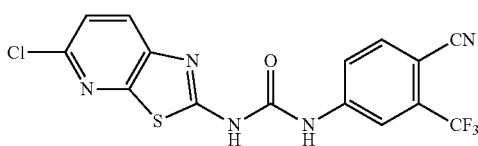
Compound 166
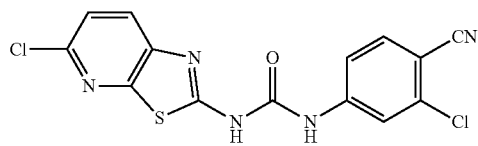
Compound 167
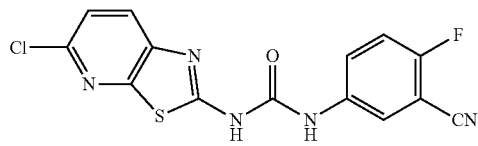
Compound 168
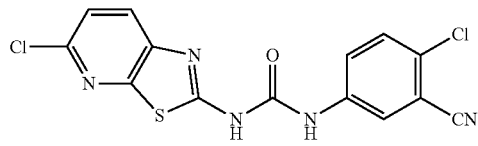
Compound 169
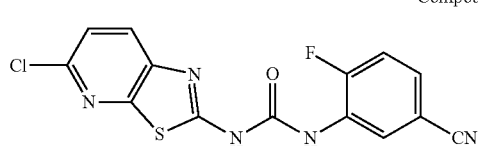
Compound 170
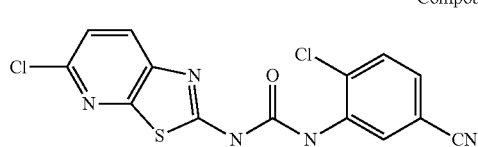
Compound 171
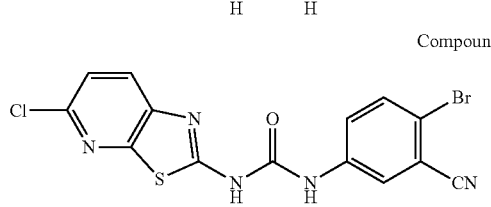
Compound 172
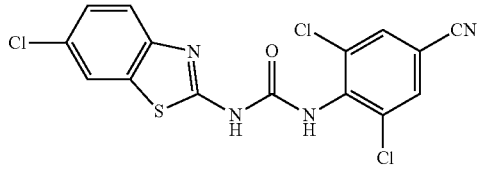
Compound 173
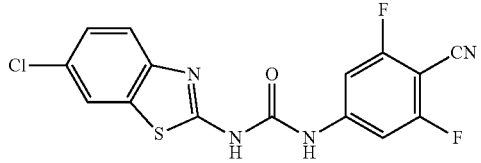
Compound 174
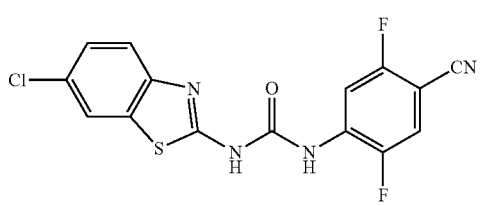
Compound 175
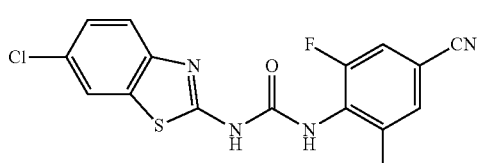
Compound 176
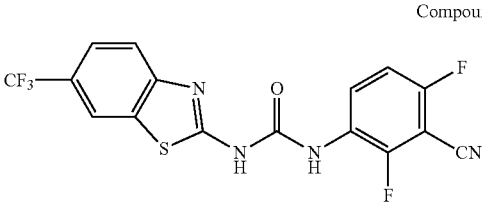
Compound 177
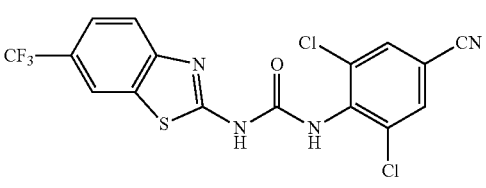
Compound 178
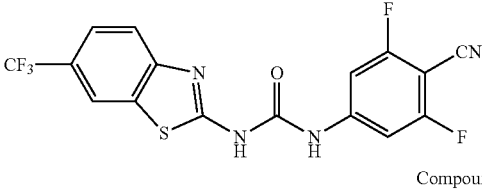
Compound 179

Compound 180
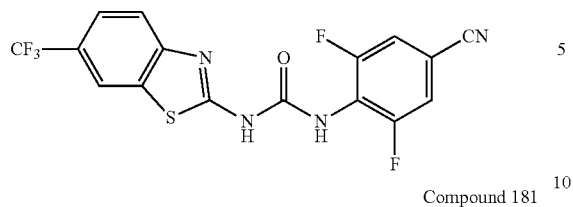
Compound 181
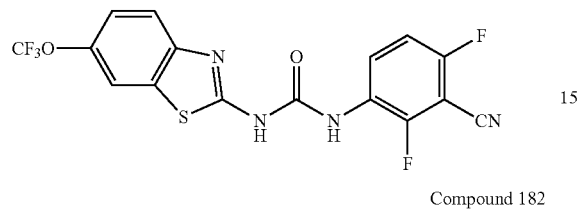
Compound 182
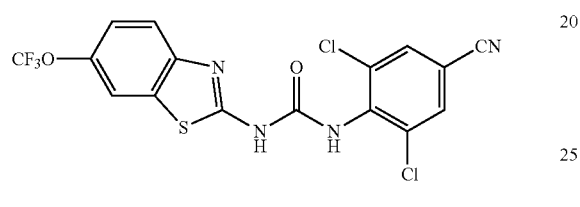
Compound 183
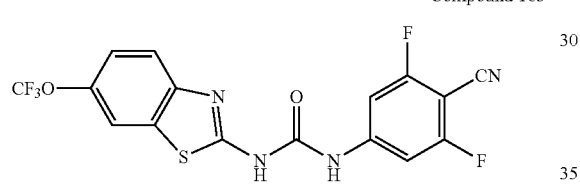
Compound 184
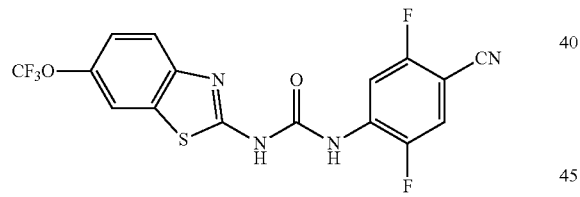
Compound 185
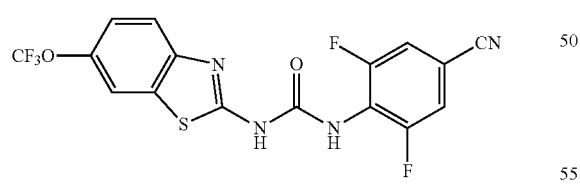
Compound 186
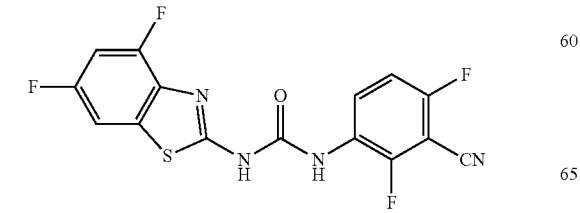
Compound 187
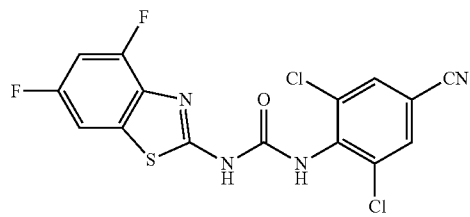
Compound 188
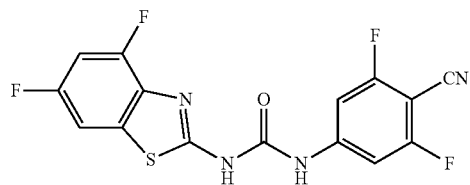
Compound 189
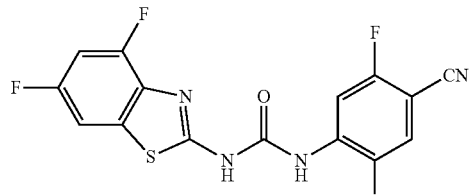
Compound 190
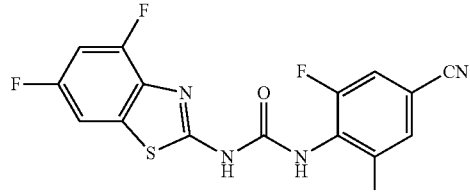
Compound 191
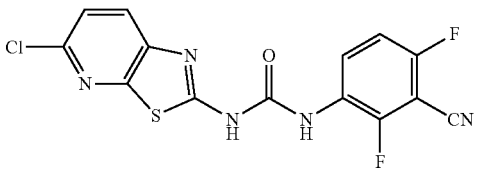
Compound 192
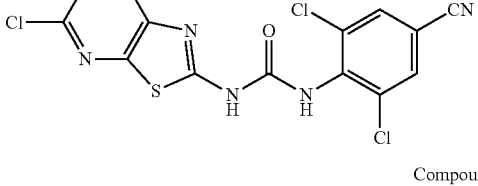
Compound 193
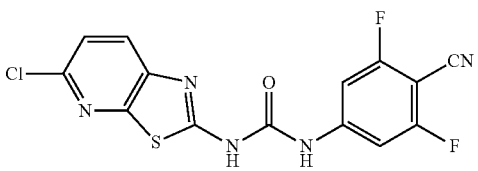

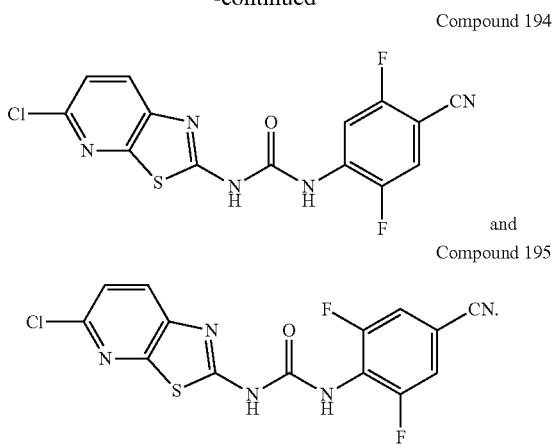

Compound 194 and

Compound 195 and combinations thereof.

In another aspect, the present invention relates to a pharmaceutical composition comprising a compound according to the present invention, and in another aspect such compositions further comprising a pharmaceutically acceptable carrier.

In another aspect, the present invention relates to a method for treating cancer comprising administering a therapeutically effective amount of a compound according to the present invention to a mammal in need thereof.

In another aspect, the present invention relates to a method for treating cancer wherein the mammal is a human.

In another aspect, the present invention relates to a compound according to the present invention in the manufacture of a medicament for treating cancer in a mammal in need thereof, and in another aspect wherein the mammal is a human.

In another aspect, the present invention relates to a method for degradation of SUMO1 protein comprising administering a therapeutically effective amount of a compound according to the present invention to a mammal in need thereof.

In another aspect, the present invention relates to a method for degradation of SUMO1 protein wherein the mammal is a human.

In another aspect, the present invention relates to a compound according to the present invention in the manufacture of a medicament for degradation of SUMO1 protein in a mammal in need thereof.

In another aspect, the present invention relates to a method for inhibiting SUMO1 comprising administering a therapeutically effective amount of a compound according to the present invention to a mammal in need thereof.

In another aspect, the present invention relates to a method for inhibiting SUMO1 wherein the mammal is a human.

In another aspect, the present invention relates to a compound according to the present invention in the manufacture of a medicament for inhibiting SUMO1 in a mammal in need thereof.

It is contemplated that for one of ordinary skill in the art, the terms "degradation of SUMO1 protein" and "inhibiting SUMO1" are used interchangeably.

These and other aspects of the present invention will become apparent from the disclosure herein.

Definitions

As used herein, the following terms and abbreviations have the indicated meanings unless expressly stated to the contrary.

The term "selective" with respect to the SUMO1 degraders or SUMO1 inhibitors of the present invention means a compound having selectively for SUMO1 over SUMO2/3.

As stated above, it is recognized that the terms "degradation of SUMO1 protein" and "inhibiting SUMO1" are used interchangeably by one of ordinary skill in the art.

The term "pharmaceutically acceptable" is used herein with respect to the compounds, compositions and salts and esters of the compounds of the present invention. The pharmaceutical compositions of the present invention comprise a therapeutically effective amount of the compounds of the present invention and a pharmaceutically acceptable carrier. These carriers can contain a wide range of excipients. Pharmaceutically acceptable carriers are those conventionally known carriers having acceptable safety profiles. The compositions are made using common formulation techniques. See, for example, *Remington's Pharmaceutical Sciences*, 17$^{th}$ edition, edited by Alfonso R. Gennaro, Mack Publishing Company, Easton, Pa., 17th edition, 1985, Regarding pharmaceutically acceptable salts, these are described below.

The term "subject" means a human patient or animal in need of treatment or intervention for cutaneous fibrosis or connective tissue disorders.

The term "therapeutically effective" means an amount of the compound of the present invention needed to provide a meaningful or demonstrable benefit, as understood by medical practitioners, to a subject, such as a human patient or animal, in need of treatment. Conditions, intended to be treated include, for example, various cancers. For example, a meaningful or demonstrable benefit can be assessed or quantified using various clinical parameters. The demonstration of a benefit can also include those provided by models, including but not limited to in vitro models, in vivo models, and animal models. An example of such a model, is a glioblastoma cell-based SUMO1 assay for drug screening and identified compounds with desired activity. Known toxicity and pharmacokinetic assays to further evaluate the compounds.

The terms "treat," "treating" or "treatment," as used herein, include alleviating, abating or ameliorating the condition, e.g. treating, or preventing or reducing the risk of contracting the condition or exhibiting the symptoms of the condition, ameliorating or preventing the underlying causes of the symptoms, inhibiting the condition, arresting the development of the condition, relieving the condition, causing regression of the condition, or stopping the symptoms of the condition, either prophylactically and/or therapeutically.

The methods of treatment using the compounds of the present invention or a pharmaceutically acceptable salt or ester thereof or the pharmaceutical compositions of the present invention, in various embodiments also include the use of the compounds or a pharmaceutically acceptable salt or ester thereof in the manufacture of a medicament for the desired treatment, such as a cancer treatment.

SUMO1 Protein Degrading or Inhibiting Compounds

As discussed above, in our earlier work, we have demonstrated that SUMO1 conjugation pathway is overactive in glioblastoma and drives the cancer formation and progression. We have also found that SUMO1 conjugation is elevated in many types of cancers. Knockdown of SUMO1 with interfering RNA inhibits the cancer formation and progression. We concluded that inhibition of SUMO1 conjugation can potentially provide a therapeutic benefit against development and progression of certain cancers.

To target SUMO1 conjugation pathway in cancers, we have demonstrated that the present invention compounds selectively induce the ubiquitination and degradation of SUMO1 but not SUMO2/3 protein and thereby inhibits SUMO1 but not SUMO2/3 conjugation. This finding of the bioactivity of these compounds as SUMO1 degraders and SUMO1 inhibitors lead to the further development of the family of benzothiazolyl urea and thiourea compounds described herein useful as anti-cancer agents.

Without limitation to only those embodiments expressly disclosed herein, and without waiver or disclaimer of any embodiments or subject matter, some embodiments comprise methods, systems and/or compositions comprised of SUMO1 protein degrading compounds of the following structure of chemical Formula I

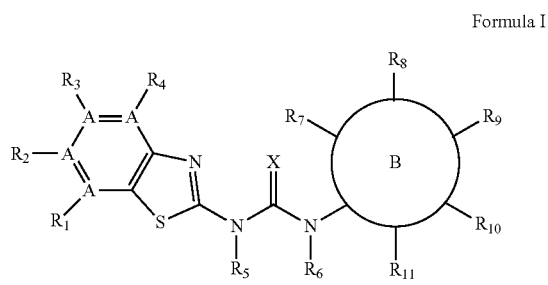

Formula I or a pharmaceutically acceptable salt or ester thereof, wherein
each A is independently selected from C or N, wherein when A is selected from N the indicated substituent $R_1$, $R_2$, $R_3$, or $R_4$ on that N is absent, and wherein no more than two A are simultaneously N;
the substituent

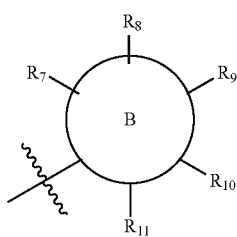

is a 5- or 6-membered aromatic or heteroaromatic ring, or 8-, 9-, or 10-membered aromatic or heteroaromatic fused bicyclic ring, having one or more substituents selected from $R_7$, $R_8$, $R_9$, $R_{10}$, and $R_{11}$;
each $R_1$, $R_2$, $R_3$, and $R_4$, when present, is independently selected from H, F, Cl, Br, I, —OH, —$OR_{12}$, —SH, —$SR_{12}$, —$NO_2$, —CN, —$NH_2$, —$NHR_{12}$, —$N(R_{12})_2$, —COOH, —$COOR_{12}$, —$C(O)NH_2$, —$C(O)NHR_{12}$, —$C(O)N(R_{12})_2$, —C(O)H, —$C(O)R_{12}$, $C_1$-$C_6$ alkyl or $C_3$-$C_6$ branched or cyclic alkyl, $C_2$-$C_6$ alkenyl or $C_3$-$C_6$ branched or cyclic alkenyl, $C_2$-$C_6$ alkynyl or $C_4$-$C_6$ branched or cyclic alkynyl, phenyl, 5- or 6-membered heteroaryl, and 8-, 9-, or 10-membered fused bicyclic aryl or heteroaryl, wherein each such $C_1$-$C_6$ alkyl or $C_3$-$C_6$ branched or cyclic alkyl, $C_2$-$C_6$ alkenyl or $C_3$-$C_6$ branched or cyclic alkenyl, $C_2$-$C_6$ alkynyl or $C_4$-$C_6$ branched or cyclic alkynyl, phenyl, 5- or 6-membered heteroaryl, and 8-, 9-, or 10-membered fused bicyclic aryl or heteroaryl, is optionally substituted with one or more $R_{13}$;
$R_5$, and $R_6$ are each independently selected from H or $C_1$-$C_6$ alkyl, alternatively $R_5$, and $R_6$ are selected from —$(CH_2)$— or —$(CH_2CH_2)$— to form a 5-membered or 6-membered ring;
each $R_7$, $R_8$, $R_9$, $R_{10}$, and $R_{11}$, when present, is independently selected from F, Cl, Br, I, —OH, —$OR_{12}$, —SH, —$SR_{12}$, —$NO_2$, —CN, —$NH_2$, —$NHR_{12}$, —$N(R_{12})_2$, —COOH, —$COOR_{12}$, —$C(O)NH_2$, —$C(O)NHR_{12}$, —$C(O)N(R_{12})_2$, —C(O)H, —$C(O)R_{12}$, $C_1$-$C_6$ alkyl or $C_3$-$C_6$ branched or cyclic alkyl, $C_2$-$C_6$ alkenyl or $C_3$-$C_6$ branched or cyclic alkenyl, $C_2$-$C_6$ alkynyl or $C_4$-$C_6$ branched or cyclic alkynyl, phenyl, 5- or 6-membered heteroaryl, and 8-, 9-, or 10-membered fused bicyclic aryl or heteroaryl, wherein each such $C_1$-$C_6$ alkyl or $C_3$-$C_6$ branched or cyclic alkyl, $C_2$-$C_6$ alkenyl or $C_3$-$C_6$ branched or cyclic alkenyl, $C_2$-$C_6$ alkynyl or $C_4$-$C_6$ branched or cyclic alkynyl, phenyl, 5- or 6-membered heteroaryl, and 8-, 9-, or 10-membered fused bicyclic aryl or heteroaryl, is optionally substituted with one or more $R_{13}$;
each $R_{12}$ is independently selected from $C_1$-$C_6$ alkyl;
each $R_{13}$ is independently selected from F, Cl, Br, I, —OH, —$OR_{14}$, —SH, —$NO_2$, —CN, —$NH_2$, —$NHR_{14}$, —$N(R_{14})_2$, —COOH, —$COOR_{14}$, —$C(O)NH_2$, —$C(O)NHR_{14}$, —$C(O)N(R_{14})_2$, —C(O)H, —$C(O)R_{14}$, $C_1$-$C_6$ alkyl or $C_3$-$C_6$ branched or cyclic alkyl, $C_2$-$C_6$ alkenyl or $C_3$-$C_6$ branched or cyclic alkenyl, $C_2$-$C_6$ alkynyl or $C_4$-$C_6$ branched or cyclic alkynyl, phenyl, 5- or 6-membered heteroaryl, and 8-, 9-, or 10-membered fused bicyclic aryl or heteroaryl;
each $R_{14}$ is independently selected from $C_1$-$C_6$ alkyl.

Without limitation to only those embodiments expressly disclosed herein, and without waiver or disclaimer of any embodiments or subject matter, some embodiments comprise methods, systems and/or compositions comprised of SUMO1 degrading compounds of the following structure of chemical Formula II.

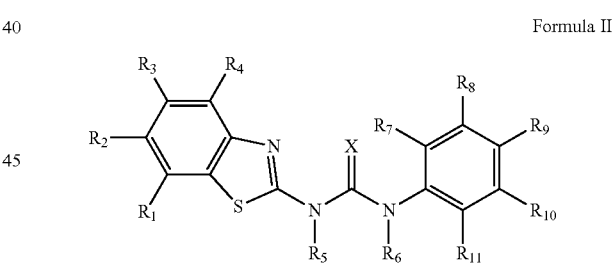

Formula II or a pharmaceutically acceptable salt or ester thereof, wherein
X is S or O,
each $R_1$, $R_2$, $R_3$, and $R_4$, is independently selected from H, F, Cl, Br, I, —OH, —$OR_{12}$, —SH, —$SR_{12}$, —$NO_2$, —CN, —$NH_2$, —$NHR_{12}$, —$N(R_{12})_2$, —COOH, —$COOR_{12}$, —$C(O)NH_2$, —$C(O)NHR_{12}$, —$C(O)N(R_{12})_2$, —C(O)H, —$C(O)R_{12}$, $C_1$-$C_6$ alkyl or $C_3$-$C_6$ branched or cyclic alkyl, $C_2$-$C_6$ alkenyl or $C_3$-$C_6$ branched or cyclic alkenyl, $C_2$-$C_6$ alkynyl or $C_4$-$C_6$ branched or cyclic alkynyl, phenyl, 5- or 6-membered heteroaryl, and 8-, 9-, or 10-membered fused bicyclic aryl or heteroaryl, wherein each such $C_1$-$C_6$ alkyl or $C_3$-$C_6$ branched or cyclic alkyl, $C_2$-$C_6$ alkenyl or $C_3$-$C_6$ branched or cyclic alkenyl, $C_2$-$C_6$ alkynyl or $C_4$-$C_6$ branched or cyclic alkynyl, phenyl, 5- or 6-membered heteroaryl, and 8-, 9-, or 10-membered fused bicyclic aryl or heteroaryl, is optionally substituted with one or more $R_{13}$;

$R_5$, and $R_6$ are each independently selected from H or $C_1$-$C_6$ alkyl, alternatively $R_6$, and $R_6$ are selected from —($CH_2$)— or —($CH_2CH_2$)— to form a 5-membered or 6-membered ring;

each $R_7$, $R_8$, $R_9$, $R_{10}$, and $R_{11}$, is independently selected from H, F, Cl, Br, I, —OH, —$OR_{12}$, —SH, —$SR_{12}$, —$NO_2$, —CN, —$NH_2$, —$NHR_{12}$, —$N(R_{12})_2$, —COOH, —$COOR_{12}$, —$C(O)NH_2$, —$C(O)NHR_{12}$, —$C(O)N(R_{12})_2$, —$C(O)H$, —$C(O)R_{12}$, $C_1$-$C_6$ alkyl or $C_3$-$C_6$ branched or cyclic alkyl, $C_2$-$C_6$ alkenyl or $C_3$-$C_6$ branched or cyclic alkenyl, $C_2$-$C_6$ alkynyl or $C_4$-$C_6$ branched or cyclic alkynyl, phenyl, 5- or 6-membered heteroaryl, and 9-, or 10-membered fused bicyclic aryl or heteroaryl, wherein each such $C_1$-$C_6$ alkyl or $C_3$-$C_6$ branched or cyclic alkyl, $C_2$-$C_6$ alkenyl or $C_3$-$C_6$ branched or cyclic alkenyl, $C_2$-$C_6$ alkynyl or $C_4$-$C_6$ branched or cyclic alkynyl, phenyl, 5- or 6-membered heteroaryl, and 8-, 9-, or 10-membered fused bicyclic aryl or heteroaryl, is optionally substituted with one or more $R_{13}$;

each $R_{12}$ is independently selected from $C_1$-$C_6$ alkyl;

each $R_{13}$ is independently selected from F, Cl, Br, I, —OH, —$OR_{14}$, —SH, —$SR_{14}$, —$NO_2$, —CN, —$NH_2$, —$NHR_{14}$, —$N(R_{14})_2$, —COOH, —$COOR_{14}$, —$C(O)NH_2$, —$C(O)NHR_{14}$, —$C(O)N(R_{14})_2$, —$C(O)H$, —$C(O)R_{14}$, $C_1$-$C_6$ alkyl or $C_3$-$C_6$ branched or cyclic alkyl, $C_2$-$C_6$ alkenyl or $C_3$-$C_6$ branched or cyclic alkenyl, $C_2$-$C_6$ alkynyl or $C_4$-$C_6$ branched or cyclic alkynyl, phenyl, 5- or 6-membered heteroaryl, and 8-, 9-, or 10-membered fused bicyclic aryl or heteroaryl;

each $R_{14}$ is independently selected from $C_1$-$C_6$ alkyl.

In addition to pharmaceutically acceptable salts or esters, the present invention also contemplates pharmaceutically acceptable metabolites, prodrugs, isomers, crystals, polymorphs, analogues, solvates, or hydrates of any compound as disclosed herein, and the use of SUMO1 degrading/inhibition compounds in the research, diagnosis, or treatment of conditions, diseases, or injuries of mammalian subjects, including but not limited to, the treatment of cancers.

In general summary, the inventors have discovered unexpectedly that, in accordance with some nonlimiting embodiments, the compounds of the present invention comprise novel therapeutic agents and methods for treatment of cancer in mammalian subjects, including but not limited to, human beings.

"Small ubiquitin-like modifier" ("SUMO") is an UB-related protein family member. SUMO conjugation, i.e. SUMOylation is a protein posttranslational modification pathway distinct from ubiquitination. There are three confirmed conjugated isoforms of SUMO: SUMO1-3, however, SUMO2 and SUMO3 are often referred to as SUMO2/3 because they differ only by three residues and cannot be distinguished by any antibodies. In contrast, SUMO1 is distinct from SUMO2/3 because it shares only about 50% amino acids homology.

The inventors have discovered that SUMO1 conjugation pathway is overactive in human glioblastoma and knockdown of SUMO1 protein inhibits the cancer formation and progression. We have also discovered that SUMO1 conjugation is overactive in many other types of cancers including breast, colorectal and lung carcinomas; and the present invention compounds can inhibit the growth of these cancers and, therefore, can be used in treating SUMO1-related cancers and other diseases.

For example, without limitation, pharmaceutical compositions of this compound (CPD1) can comprise a molecular weight 348 g/mol and the log P value 3.7. We have shown that the pharmacokinetics and tissue distribution of CPD1 are sufficient for degrading SUMO1 protein in mouse cancer xenografts with no toxicity to normal tissues or side effects on mice through intraperitoneal administration. The compound can cross the blood brain barrier in distribution in brain tumors for treatment of brain cancers such as glioblastoma.

The inventors have discovered unexpectedly that treatment with CPD1 and CPD24 induces the ubiquitination and degradation of SUMO1 protein and inhibits the cell growth of human cancer cells at least of brain, breast, blood, colorectal, lung, ovarian, prostate, renal, and melanocyte origin. Administration of CPD1 or CPD24 through intraperitoneal injections suppresses the cancer xenograft growth and prolongs the survival of intracranial brain xenograft bearing mice.

Some embodiments comprise, without limitation, our discovery that: (1) SUMO1 conjugation is elevated in human cancer and drives cancer formation and progression, and this conjugation can be targeted by small molecules for cancer therapy; and (2) SUMO1 degrading compounds/SUMO1 degraders comprise anticancer drugs through induction of SUMO1 protein ubiquitination and degradation and for clinical treatment of SUMO1-related diseases including cancers. In accordance with some embodiments, SUMO1 degrading compounds, but not limited to, Compounds 1-125, derivatives, and compounds with similar compositions, can be used to target SUMO1 pathway as therapeutic agents.

The term "halogen" refers to fluoro, chloro, bromo and iodo. In particular embodiments, "halogen" refers to fluoro and chloro.

Without limitation and without waiver or disclaimer of any embodiments or subject matter, some embodiments comprise SUMO1 protein degrader/SUMO1 inhibitor, agents which increase any SUMO1 degrader/SUMO1 inhibitor, and agents which deliver any SUMO1 degrader/SUMO1 inhibitor (all collectively "SUMO1 degrader/SUMO1 inhibitor agent(s)"), to prevent, control, or alleviate mammalian illness or injury, including without limitation, cancer(s), through the selective administration of such SUMO1 degrader/SUMO1 inhibitor agent(s). In accordance with some embodiments, without limitation, one may inhibit such illness or injury through SUMO1 degrader/SUMO1 inhibitor agent administration for a finite interval of time, thereby limiting the development or course of such illness or injury.

Embodiments may also comprise SUMO1 degrader/SUMO1 inhibitor agents described by Markush group(s), inclusively and/or by exclusion of one or more of such agent(s) from any of such Markush group(s).

Methods of Use and Administration

In some nonlimiting embodiments, SUMO1 degrader/SUMO1 inhibitor, agents which increase SUMO1 degrader/SUMO1 inhibitor, and/or agents which deliver SUMO1 degrader/SUMO1 inhibitor, may be used as therapies for the prevention and treatment of SUMO1-mediated diseases, for example, cancers. Thus, in accordance with some nonlimiting embodiments, compounds of the present invention can be administered to a patient before or after the onset of injury or disease to reduce the symptomatology and pathological effects associated with a SUMO1-mediated disease or disorder, for example, cancer. In some embodiments, compounds of the present invention, or a pharmaceutically acceptable salt, metabolite, prodrug, isomer, crystal, polymorph, analog, solvate, or hydrate thereof can be administered to a patient before or after the onset of injury or disease to reduce the symptomatology and pathological effects associated with a SUMO1-mediated disease or disorder, for example, cancer.

Formulations

It is contemplated that, once identified, the active molecules of the invention can be incorporated into any suitable carrier prior to use to provide a pharmaceutical composition. The dose of active molecule, mode of administration and use of suitable carrier will depend upon the intended recipient and target organism. The formulations, both for veterinary and for human medical use, of compounds according to the present invention typically include such compounds in association with a pharmaceutically acceptable carrier.

The carrier(s) should be "acceptable" in the sense of being compatible with the other ingredients of the formulations and not deleterious to the recipient. Pharmaceutically acceptable carriers, in this regard, are intended to include any and all solvents, dispersion media, coatings, anti-bacterial and anti-fungal agents, isotonic and absorption delaying agents, and the like, compatible with pharmaceutical administration. The use of such media and agents for pharmaceutically active substances is known in the art. Except insofar as any conventional media or agent is incompatible with the active compound, use thereof in the compositions is contemplated. Supplementary active compounds (identified or designed according to the invention and/or known in the art) also can be incorporated into the compositions. The formulations may conveniently be presented in dosage unit form and may be prepared by any of the methods well known in the art of pharmacy/microbiology. In general, some formulations are prepared by bringing the compound into association with a liquid carrier or a finely divided solid carrier or both, and then, if necessary, shaping the product into the desired formulation.

A pharmaceutical composition of the invention should be formulated to be compatible with its intended route of administration. Examples of routes of administration include oral or parenteral, for example, intravenous, intradermal, inhalation, transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide.

Useful solutions for oral or parenteral administration can be prepared by any of the methods well known in the pharmaceutical art, described, for example, in Remington's Pharmaceutical Sciences, (Gennaro, A., ed.), Mack Pub., (1990), Formulations for parenteral administration can also include glycocholate for buccal administration, methoxysalicylate for rectal administration, or citric acid for vaginal administration. The parenteral preparation can be enclosed in ampoules, disposable syringes or multiple dose vials made of glass or plastic. Suppositories for rectal administration also can be prepared by mixing the drug with a non-irritating excipient such as cocoa butter, other glycerides, or other compositions which are solid at room temperature and liquid at body temperatures. Formulations also can include, for example, polyalkylene glycols such as polyethylene glycol, oils of vegetable origin, and hydrogenated naphthalenes, Formulations for direct administration can include glycerol and other compositions of high viscosity. Other potentially useful parenteral carriers for these drugs include ethylene-vinyl acetate copolymer particles, osmotic pumps, implantable infusion systems, and liposomes.

Formulations of the present invention suitable for oral administration may be in the form of: discrete units such as capsules, gelatin capsules, sachets, tablets, troches, or lozenges, each containing a predetermined amount of the drug; a powder or granular composition; a solution or a suspension in an aqueous liquid or non-aqueous liquid; or an oil-in-water emulsion or a water-in-oil emulsion. The drug may also be administered in the form of a bolus, electuary or paste. A tablet may be made by compressing or moulding the drug optionally with one or more accessory ingredients, Compressed tablets may be prepared by compressing, in a suitable machine, the drug in a free-flowing form such as a powder or granules, optionally mixed by a binder, lubricant, inert diluent, surface active or dispersing agent. Moulded tablets may be made by moulding, in a suitable machine, a mixture of the powdered drug and suitable carrier moistened with an inert liquid diluent.

The tablets, pills, capsules, troches and the like can contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). It should be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filter sterilization. Generally, dispersions are prepared by incorporating the active compound into a sterile vehicle which contains a basic dispersion medium and the required other ingredients from those enumerated above. In the case of sterile powders for the preparation of sterile injectable solutions, methods of preparation include vacuum drying and freeze-drying which yields a powder of the active ingredient plus any additional desired ingredient from a previously sterile-filtered solution thereof.

Oral or parenteral compositions can be formulated in dosage unit form for ease of administration and uniformity of dosage. Dosage unit form refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals. Furthermore, administration can be by periodic injections of a bolus, or can be made more continuous by intravenous, intramuscular or intraperitoneal administration from an external reservoir (e.g., an intravenous bag).

EXAMPLES

The following examples further describe and demonstrate embodiments within the scope of the present invention. The Examples are given solely for purpose of illustration and are not to be construed as limitations of the present invention, as many variations thereof are possible without departing from the spirit and scope of the invention.

Example 1

Table 1 shows $IC_{50}$ values for compounds of the present invention on inhibition of cancer cell growth through selective degradation of SUMO1 protein and inhibition of SUMO1 conjugation. Each of the compounds was used to treat the cancer LN229 cells and examined first by western and dot blot assays for the degradation of SUMO1 protein and then by cell viability assay for the $IC_{50}$ values of anticancer activity.

TABLE 1

| Compound Number | Inhibition of Cancer Cell Growth ($IC_{50}$) |
|---|---|
| 1 | +++ |
| 2 | +++ |
| 3 | +++ |
| 4 | +++ |
| 5 | +++ |
| 6 | +++ |
| 7 | + |
| 8 | + |
| 9 | + |
| 10 | +++ |
| 11 | + |
| 12 | ++ |
| 13 | + |
| 14 | ++ |
| 15 | + |
| 16 | + |
| 17 | + |
| 18 | + |
| 19 | + |
| 20 | + |
| 21 | + |
| 22 | ++ |
| 23 | +++ |
| 24 | +++ |
| 25 | + |
| 26 | ++ |

TABLE 1-continued

| Compound Number | Inhibition of Cancer Cell Growth ($IC_{50}$) |
|---|---|
| 27 | + |
| 28 | ++ |
| 29 | + |
| 30 | +++ |
| 31 | +++ |
| 32 | +++ |
| 33 | +++ |
| 34 | +++ |
| 35 | + |
| 36 | +++ |
| 37 | +++ |
| 38 | +++ |
| 39 | +++ |
| 40 | + |
| 41 | +++ |
| 42 | +++ |
| 43 | ++ |
| 44 | + |
| 45 | +++ |
| 46 | + |
| 47 | + |
| 48 | ++ |
| 49 | ++ |
| 50 | ++ |
| 51 | ++ |
| 52 | + |
| 53 | +++ |
| 54 | + |
| 55 | ++ |
| 56 | + |
| 57 | + |
| 58 | ++ |
| 59 | ++ |
| 60 | + |
| 61 | +++ |
| 62 | +++ |
| 63 | ++ |
| 64 | + |
| 65 | + |
| 66 | +++ |
| 67 | ++ |
| 68 | + |
| 69 | ++ |
| 70 | +++ |
| 71 | +++ |
| 72 | +++ |
| 73 | ++ |
| 74 | +++ |
| 75 | + |
| 76 | + |
| 77 | + |
| 79 | + |
| 80 | + |
| 81 | + |
| 82 | ++ |
| 83 | +++ |
| 84 | +++ |
| 85 | +++ |
| 86 | +++ |
| 87 | +++ |
| 88 | ++ |
| 89 | + |
| 90 | + |
| 91 | +++ |
| 92 | +++ |
| 93 | +++ |
| 94 | +++ |
| 95 | + |
| 96 | +++ |
| 97 | ++ |
| 98 | +++ |
| 99 | +++ |
| 100 | +++ |
| 101 | +++ |
| 102 | +++ |
| 103 | +++ |
| 104 | +++ |

TABLE 1-continued

| Compound Number | Inhibition of Cancer Cell Growth (IC$_{50}$) |
|---|---|
| 105 | +++ |
| 106 | ++ |
| 107 | +++ |
| 108 | + |
| 109 | + |
| 110 | ++ |
| 111 | + |
| 112 | + |
| 113 | +++ |
| 114 | ++ |
| 115 | +++ |
| 116 | +++ |
| 117 | +++ |
| 118 | +++ |
| 119 | +++ |
| 120 | +++ |
| 121 | + |
| 122 | +++ |
| 123 | ++ |

+++ IC$_{50}$ ≤ 5 uM
++ IC$_{50}$ ≤ 20 uM
+ IC$_{50}$ > 20 uM

Based on the IC$_{50}$ values these compounds are useful for administration to a human patient or animal for the treatment of a cancer.

Example 2

SUMO is an UB-like protein family member that is attached to substrate proteins and modifies the protein cellular functions. Human genome encodes four isoforms of SUMO: SUMO1-4; however, SUMO4 cannot be conjugated and SUMO2 and SUMO3 are commonly referred to as SUMO2/3 because they differ only by three amino acids and cannot be distinguished by any antibodies. In contrast, SUMO1 is distinct from SUMO2/3 because they share only 50% amino acids homology. SUMO is translated as an immature precursor that is processed by a protease to generate a mature form for conjugation. The mature SUMO has a C-terminal GG motif that is linked to a lysine residue of a substrate protein through catalytic reactions mediated by the SAE1/2 and UBC9, The conjugated SUMO is removed by a protease and becomes the free mature form of SUMO for another SUMOylation cycle, (See FIG. 1.)

In vitro biochemical reactions and in vivo cell-based assays are two mainstays in drug screening of small molecules. While in vitro reactions may identify proteins or reactions-targeted compounds in a high-throughput fashion, they suffer several issues: a) proteins/reactions used in in vitro screenings may not represent proteins and/or reactions in targeted cells and b) in vitro assays provide no information on the cell permeability of compounds. In contrast, cell-based assays are tedious and time consuming but they represent the responses of targeted cells and provide information on cell permeability of compounds.

In addition, in vitro SUMOylation methodologies currently available cannot distinguish between SUMO1 and SUMO2/3 conjugation and all in vitro SUMOylation drug screens have failed to identify any selective SUMO1 inhibiting compounds. In our previous studies, we have established cancer cell-based western blot assays to distinguish between SUMO1 and SUMO2/3 conjugation. Accordingly, we used this cancer cell-based denatured western blot assays in drug screening of the NCI diversity Set IV compounds library and identified compound 1 (CPD1) of the present invention.

Figure 2A:
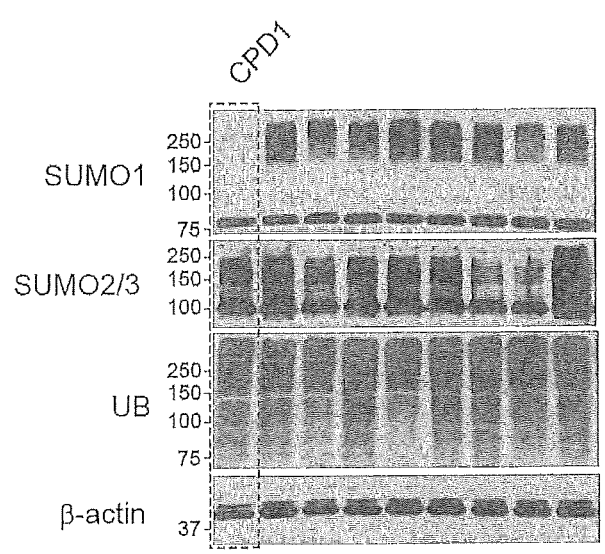
FIGS. 2A through 2C show experimental evidence that a representative compound provides proof of concept by inducing SUMO1 protein degradation through cancer cell-based drug screening.
Figure 2B:
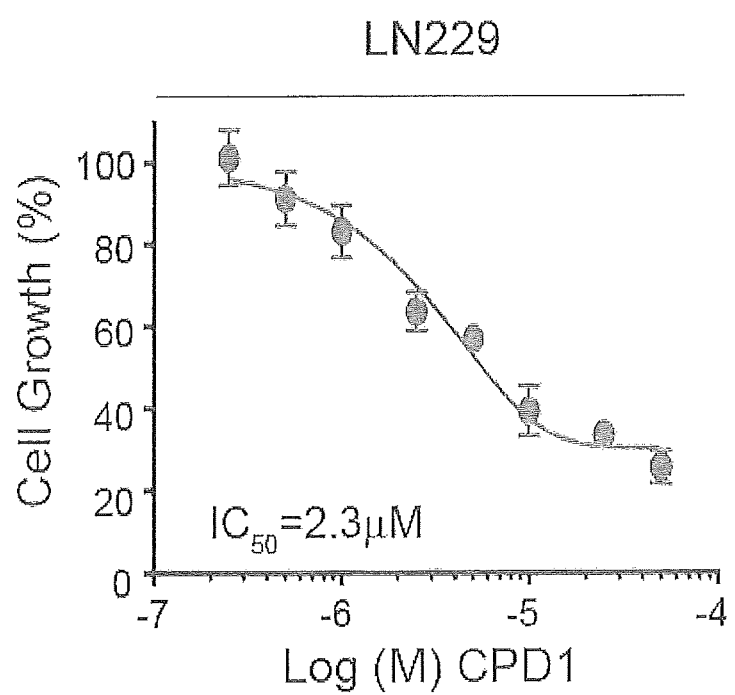
Figure 2C:
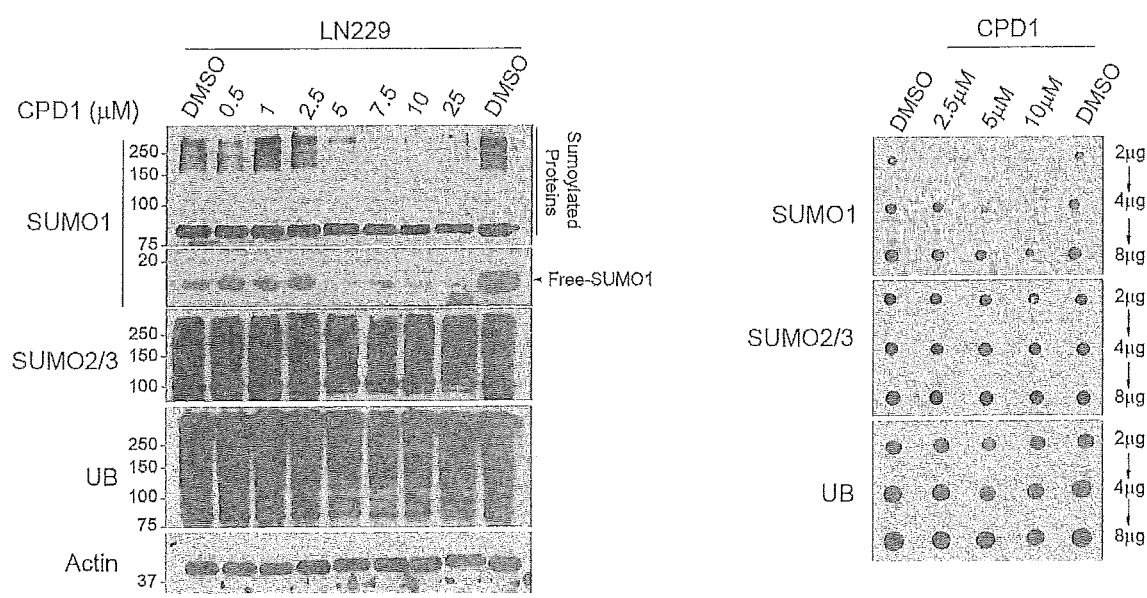

The glioblastoma LN229 cells were treated with each of compounds from the NCI Diversity Set IV library and examined by western blot assays using the antibodies to SUMO1, SUMO2/3, UB and β-actin, which identified the hit compound 1 (CPD1) selectively inhibiting the conjugation of SUMO1 but not SUMO2/3 or UB (FIG. 2A). LN229 cell were treated with a series of dilutions of CPD1 and examined by cell viability assay for cell growth inhibition (FIG. 2B). The treated LN229 cells were also analyzed by western blotting for detection of the conjugate and free form of SUMO1 protein and dot blotting for total levels of SUMO1 protein, showing that CPD1 treatment reduces the conjugated, free form and total levels of SUMO1 proteins (FIG. 2C). Therefore, CPD1 acts as the degrader of SUMO1 protein and inhibitor of SUMO1 conjugation in cancer cells.

Example 3

Figure 3A:
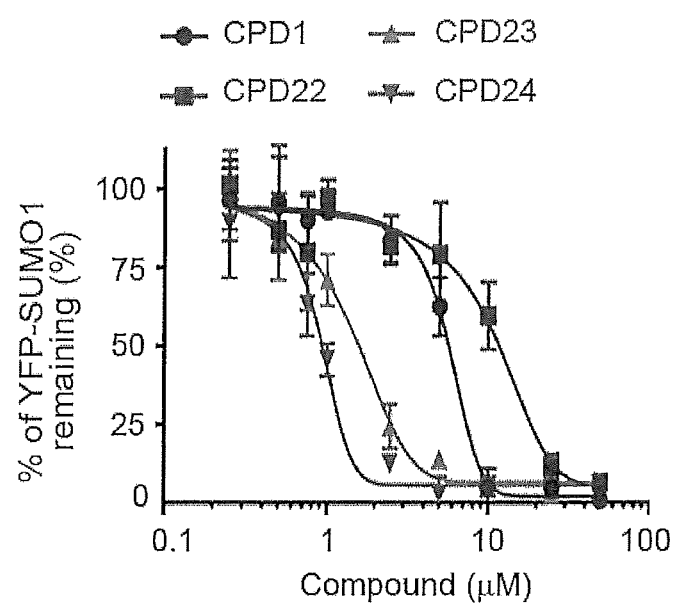
FIGS. 3A and 3B show data for representative compounds CPD1, CPD22, CPD23, and CPD24 identified through structure-activity relationship studies of CPD1 derivatives.
Figure 3B:
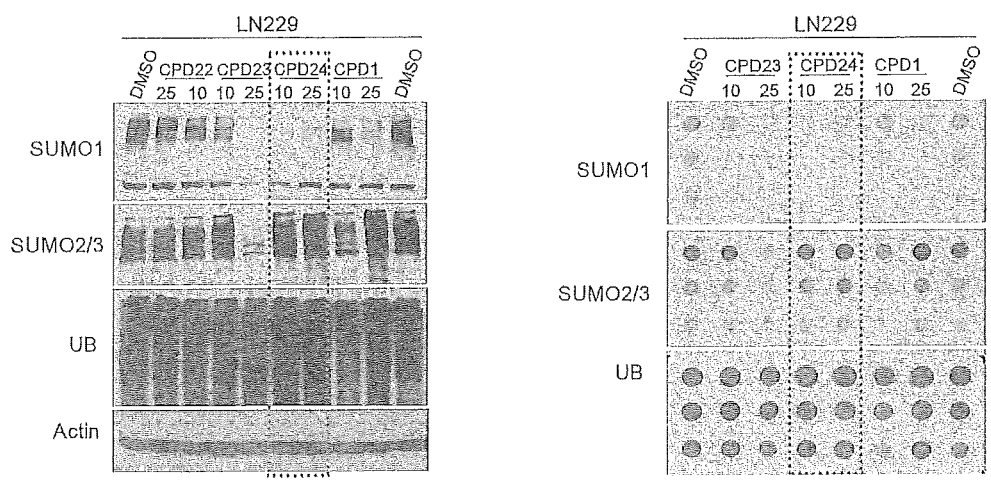

Through structure-activity relationship studies, we designed, synthesized and optimized more potent active compounds from CPD1 derivatives. The representative compounds were analyzed by cell viability assay in treatment of LN229 cells, showing that compound 24 (CPD24) is much more potent in inhibition of the cell growth (FIG. 3A). LN229 cells were treated with each of the compounds and analyzed by western and dot blot assays, which shows that the compound treatment reduces SUMO1 conjugation and total levels of SUMO1 protein (FIG. 3B). The data indicate that, like CPD1, the lead compounds act as the degraders of SUMO1 protein and inhibitors of SUMO1 conjugation in cancer cells.

Example 4

Figure 4A:
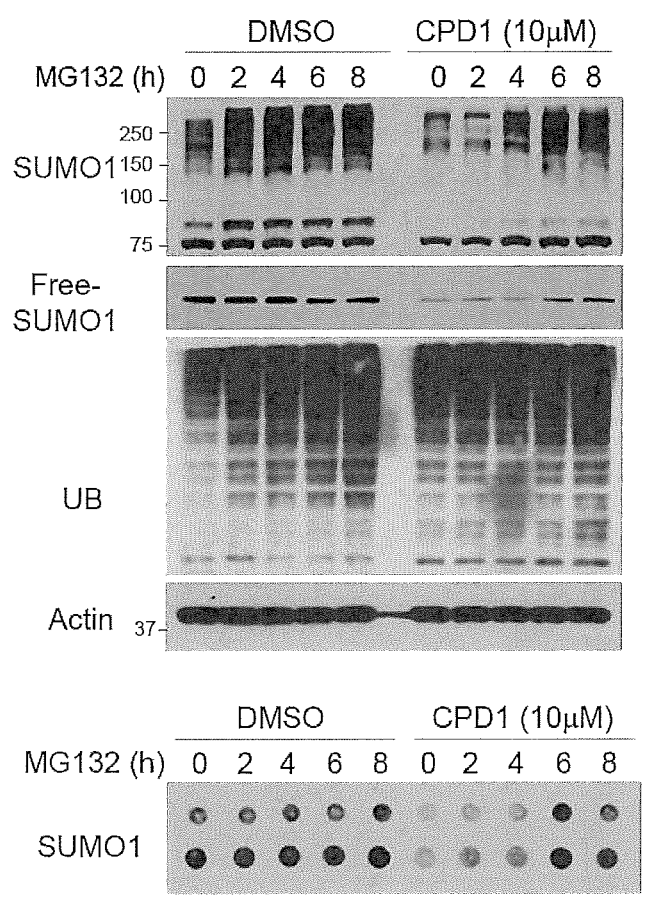
FIGS. 4A through 4C illustrates data for the mechanisms of drug action through induction of ubiquitination and degradation of SUMO1 protein.
Figure 4B:
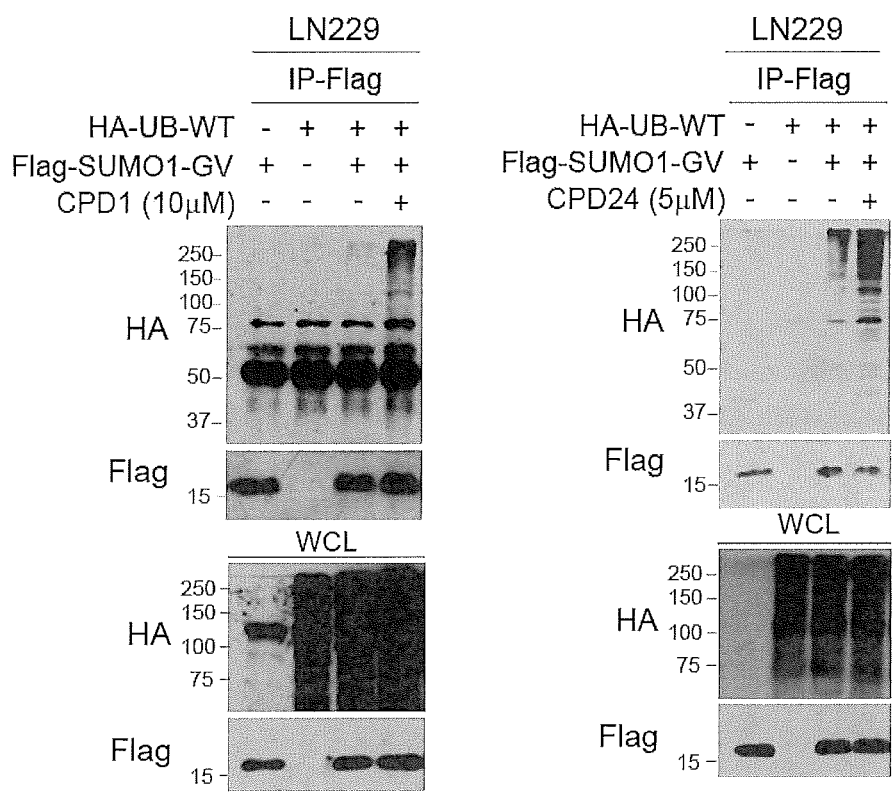
Figure 4C:
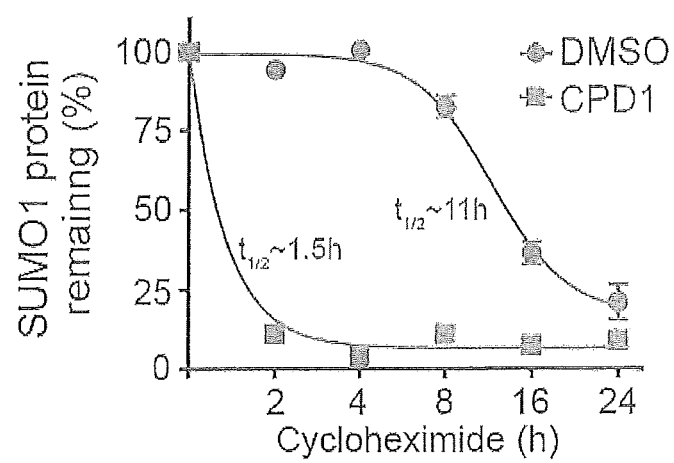

In studies of the mechanisms of drug action, we found that the compounds induce ubiquitination and degradation of SUMO1 protein and thereby inhibits SUMO1 conjugation in cancer cells. For instance, LN229 cells were treated with CPD1, followed by the 26s proteasome inhibitor MG132 and analyzed by western blotting detecting conjugated and free SUMO1 protein and dot blotting for the total levels of SUMO1 protein; the results indicate that MG132 treatment prevents CPD1-induced degradation of SUMO1 protein (FIG. 4A). The non-conjugated Flag-tagged SUMO1 (Flag-SUMO1-GV) and the HA-tagged wild type (WT) UB (HA-UB-WT) were co-transfected in LN229 cells. The cells were treated with CPD1 or CPD24, Flag-SUMO was isolated through immunoprecipitation using Flag antibodies and analyzed by western blot assays; the data show that the compound treatment results in the poly-ubiquitination of SUMO1 protein (FIG. 4B). The half-life of SUMO1 protein was analyzed in LN229 cells under the treatment of CPD1, showing that the compound treatment reduces the half-life of SUMO1 protein from 11 hours to 1.5 hour (FIG. 4C). Taken together, the data indicate that the compound treatment leads to SUMO1 protein ubiquitination and degradation and thereby inhibition of SUMO1 conjugation Example 5

Figure 5A:
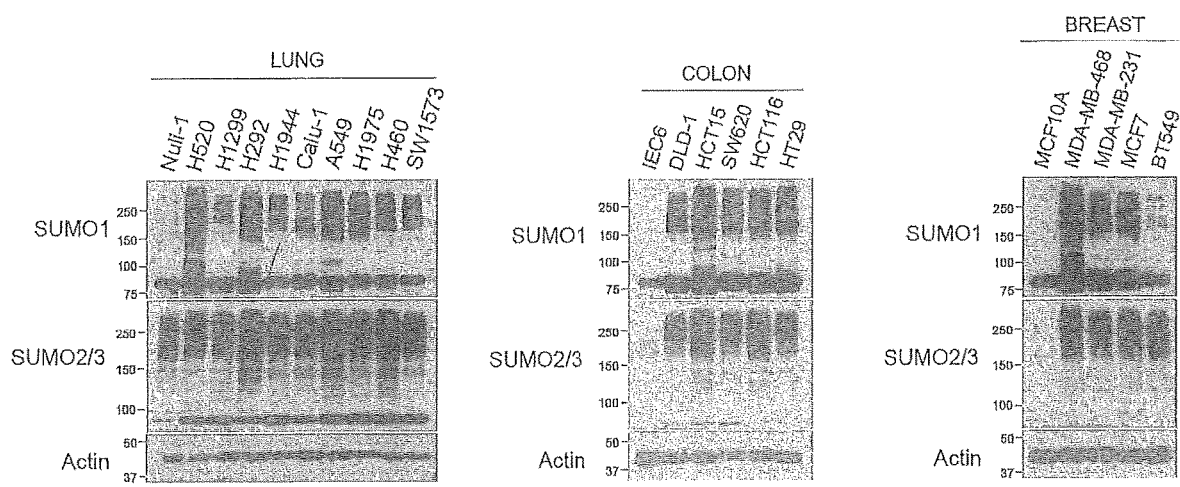
FIGS. 5A through 5D shows data for the bioactivity of the compounds against various types of cancer cells.
Figure 5B:
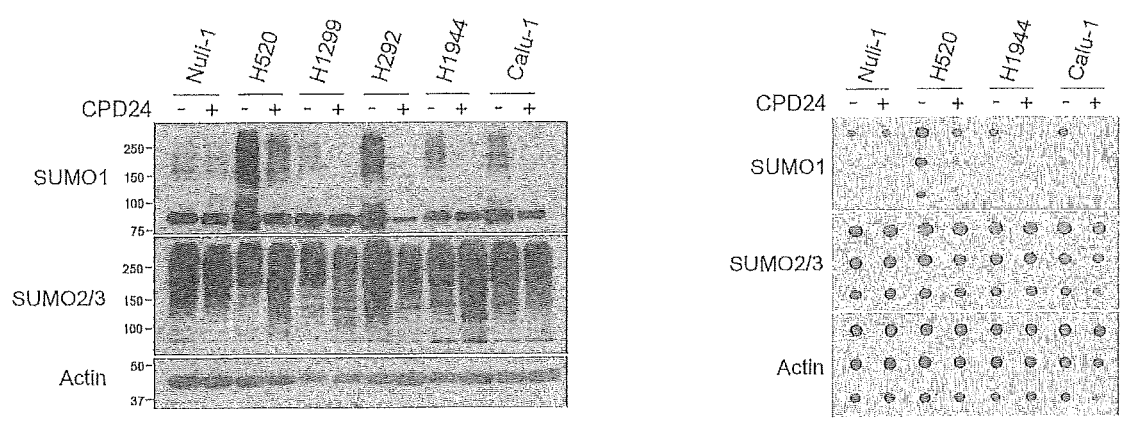
Figure 5C:
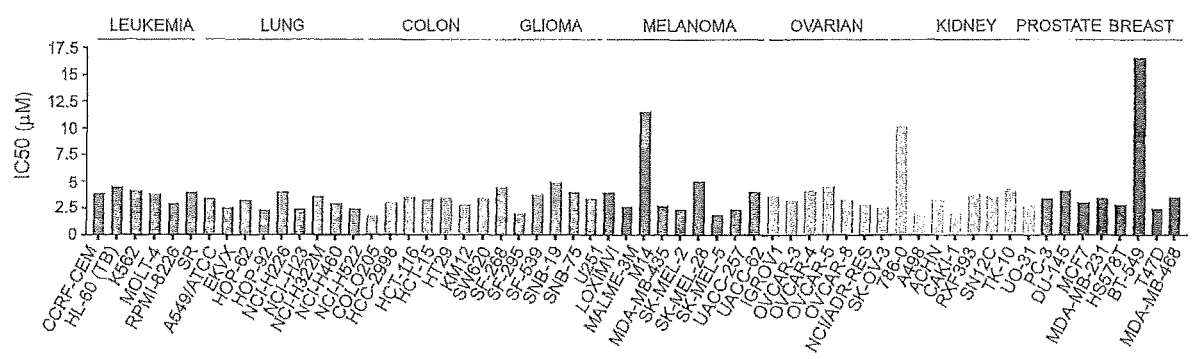
Figure 5D:
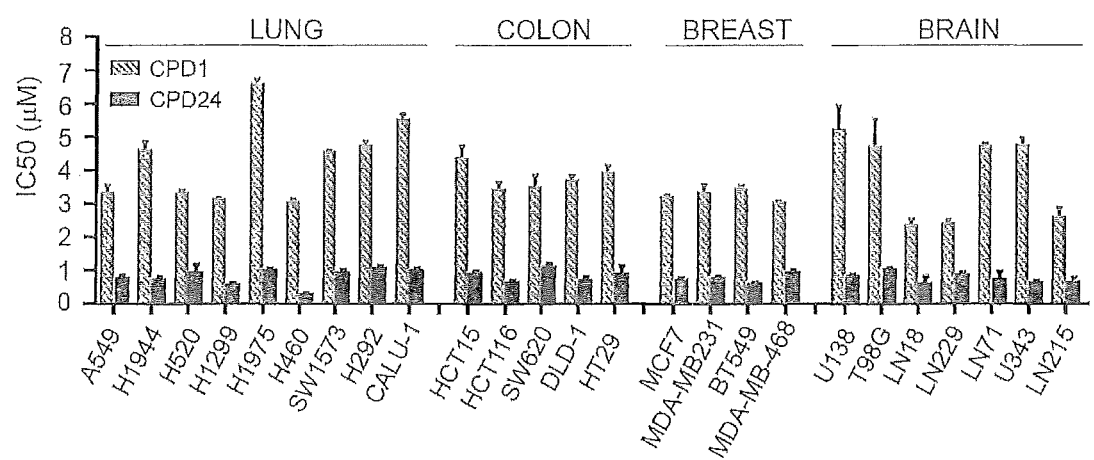

In determination of the compound bioactivity, we first found that normal epithelial cells from breast, colon and lung have barely detected levels of SUMO1 conjugation; in contrast, however, cancer cells of these organs show markedly elevated SUMO1 conjugation (FIG. 5A). Western and dot blot analysis of normal and cancer cells under CPD24 treatment show that the treatment reduces SUMO1 conjugation and total levels of SUMO1 protein only in cancer cells (FIG. 5B). The cell growth analysis of the NCI-60 panel cancer cell lines shows that CPD1 treatment significantly inhibits the cell growth of breast, colon, lung, kidney, ovarian, prostate, skin (melanocytic) and blood (leukemic) cancers (FIG. 5C). The $IC_{50}$ values of cell viability assay show that the lead compound CPD24 is more potent than the hit compound CDP1 in inhibition of twenty-five lung, colon, breast and brain cancer cell lines (FIG. 5D).

Example 6

Figure 6A:
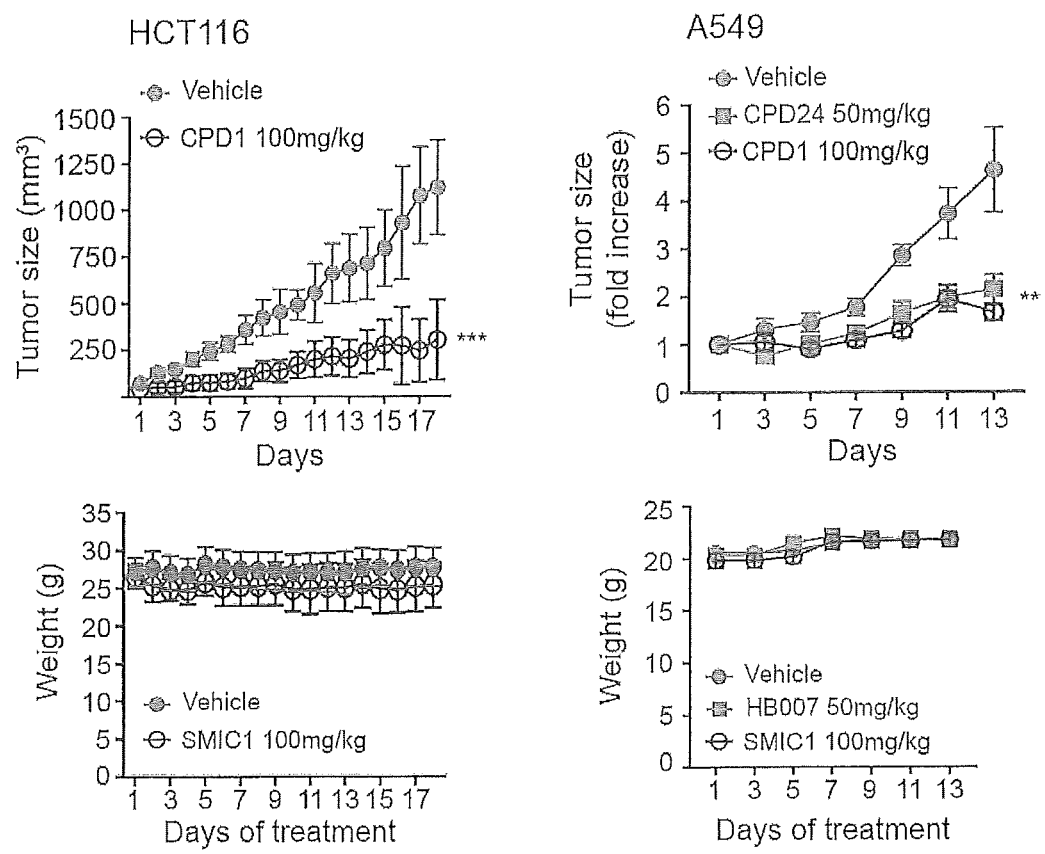
FIGS. 6A through 6C shows the therapeutic efficacy of the compounds in the treatment of cancer xenografts in mice.
Figure 6B:
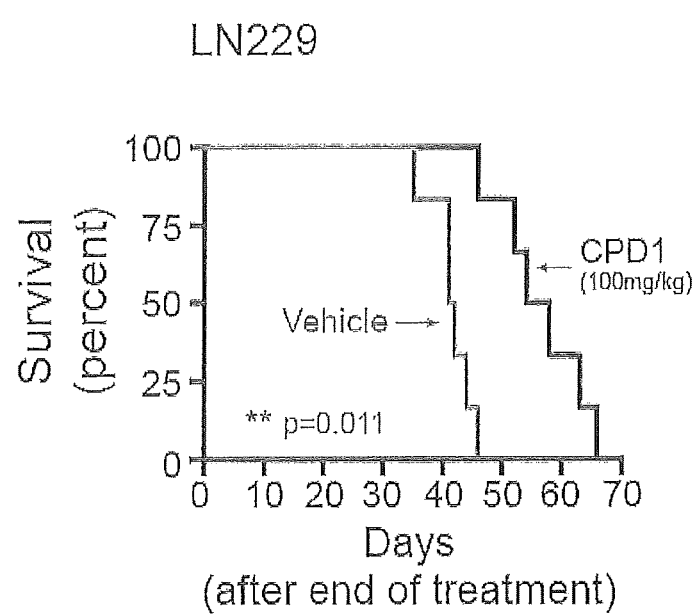
Figure 6C:
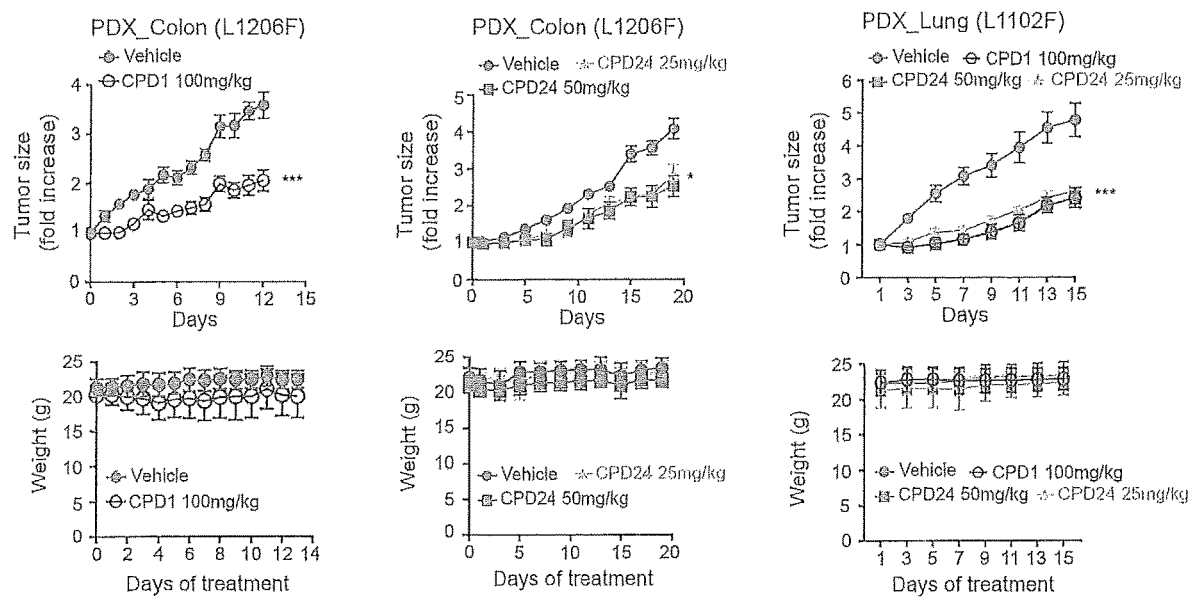

For the therapeutic effects of the compounds, we examined the effects of CPD1 and CPD24 on various types of cancer xenografts in mice. Nude mice bearing subcutaneous xenografts of colon HCT116 and lung A549 cancer cell line were treated with each compound and the data show that the treatment significantly suppressed xenograft progression (FIG. 6A). NOD/SCID mice bearing intracranial brain xenografts of glioblastoma LN229 cell line were treated with CPD1. Kaplan Meier survival analysis shows that the treatment increases the survival of xenograft mice (FIG. 6B). Patient derived xenografts (PDXs) of human colon cancer and lung cancer were treated with CPD1 or CPD24; the data show that the treatment significantly suppressed xenograft progression with CPD24 being more potent (FIG. 6C). Across all xenograft mice employed, CPD1 and CPD24 were well tolerated over the treatment period with no clinical signs of lethargy, ataxia, paralysis, seizure or weight loss (FIG. 6A, C).

Example 7: Synthesis and Characterization

General Synthetic Methods: The compounds of the invention can be prepared by the methods described below. In each of the schemes below, the groups $R^1$ to $R^{11}$ are as defined above for general Formula I or Formula II unless noted. Optimum reaction conditions and reaction times may vary depending on the particular reactants used. Unless otherwise specified, solvents, temperatures, pressures and other reaction conditions may be readily selected by one of ordinary skill in the art. Specific procedures are provided in the Synthetic Examples section. Typically, the reaction progress can be monitored by thin layer chromatography (TLC) or HPLC-MS if desired. Intermediates and products may be purified by chromatography on silica gel, recrystallization, HPLC and/or reverse phase HPLC.

Starting materials and reagents are either commercially available or may be prepared by one skilled in the art using methods described in the chemical literature and in the Synthetic Examples section below.

Preparation of Compound 24: 1-(3-chlorophenyl)-3-(6-cyano-1,3-benzothiazol-2-yl)urea

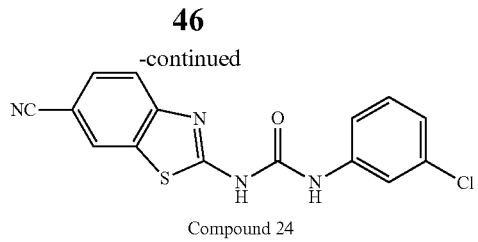

Compound 24

To a solution of 2-amino-1,3-benzothiazole-6-carbonitrile (200 mg, 1.14 mmol) in THF (8 mL) was added 3-chlorophenyl isocyanate (209 mg, 1.37 mmol) at room temperature. The solution was stirred at the same temperature for 24 hours. The solution was cooled under an ice-bath and the solid that precipitated out from the solution was collected by filtration. The solid was dried under vacuum to remove excess solvent. The solid was added to a boiling EtOH solution (10 mL) and was stirred at the same temperature for 30 minutes. The solution was cooled down to room temperature and the solid was collected by filtration. The resulting solid was washed with cold EtOH (10 mL) and was dried under vacuum. The yellow solid was confirmed to be the title product (220 mg, 60%). LCMS (ESMS): m/z: 329 ($M^+$+1)

Preparation of Compound 26: 2-(4-chlorophenyl)-N-(6-nitro-1,3-benzothiazol-2-yl)acetamide

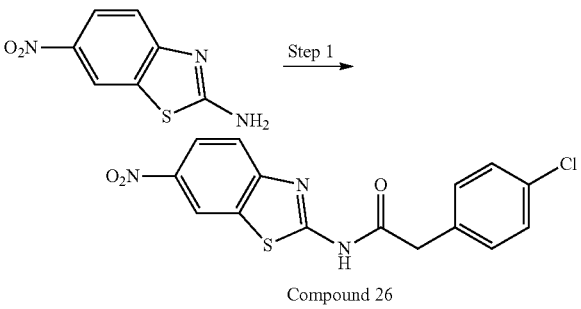

Compound 26

To a solution of 6-nitro-1,3-benzothiazol-2-amine (200 mg, 1.03 mmol) in THF (10 mL) were added triethylamine (0.3 mL, 3.09 mmol) and 4-chlorophenylacetyl chloride (232 mg, 1.23 mmol) at 0 C. The solution was allowed to warm to room temperature and was stirred for 4 hours. Ice water (10 mL) was added and the solution was extracted with EtOAc (10 mL×3). The combined organic layer was dried with $MgSO_4$ and was filtered. The filtrate was concentrated and the residue was purified by silica gel flash column chromatography with 10% EtOAc in Hexane as the eluent to afford the title product as an off-white solid (62 mg, 18%). LCMS (ESMS): m/z: 348 ($M^+$+1)

Preparation of Compounds 31 and 32: 1-(6-cyano-1,3-benzothiazol-2-yl)-3-[3-(4-fluorophenyl)phenyl]urea -continued

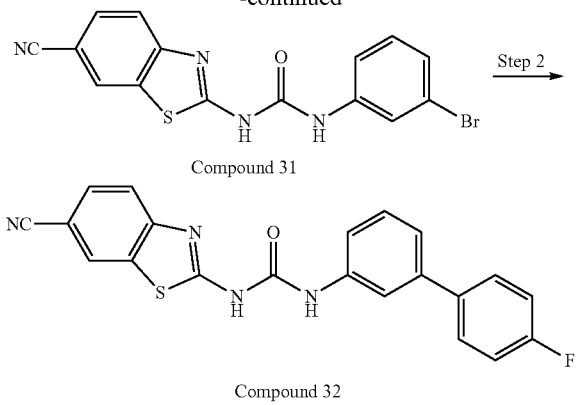

Compound 31

Compound 32

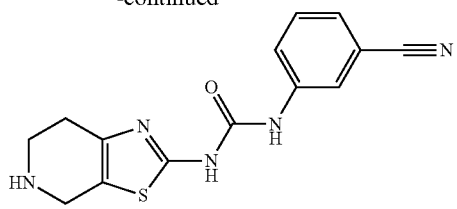

Step 1:

To a solution of 2-amino-1,3-benzothiazole-6-carbonitrile (200 mg, 1.14 mmol) in THF (8 mL) was added 3-bromophenyl isocyanate (226 mg, 1.14 mmol) at room temperature. The solution was stirred at the same temperature for 24 hours. The solution was cooled under an ice-bath and the solid that precipitated out from the solution was collected by filtration. The solid was dried under vacuum to remove excess solvent. The solid was added to a boiling EtOH solution (10 mL) and was stirred at the same temperature for 30 minutes. The solution was cooled down to room temperature and the solid was collected by filtration. The resulting solid was washed with cold EtOH (10 mL) and was dried under vacuum. The yellow solid was confirmed to be 1-(3-bromophenyl)-3-(6-cyano-1,3-benzothiazol-2-yl)urea (Compound 31) (300 mg, 71%). LCMS (ESMS): m/z: 372 ($M^++1$)

Step 2:

To a solution of 1-(3-bromophenyl)-3-(6-cyano-1,3-benzothiazol-2-yl)urea (100 mg, 0.27 mmol) in DMF (5 mL) and $H_2O$ (0.5 mL) were added 4-fluorophenylboronic acid (55.6 mg, 0.4 mmol), Pd(PPh$_3$)$_4$ (31 mg, 0.027 mmol) and cesium carbonate (21.6 mg, 0.54 mmol) at room temperature. The mixture was heated to 85 C for 12 hours. The mixture was cooled down and was poured into a water solution (20 mL). The solution was extracted with EtOAc (10 mL×3) and the combined organic layer was dried with MgSO$_4$. The mixture was filtered and the filtrate was concentrated under reduced pressure. The residue was purified by silica gel flash column chromatograph with 10% EtOAc in Hexane as the eluent to afford the title compound as a white solid (40 mg, 38%). LCMS (ESMS): m/z: 389 ($M^++1$).

Preparation of Compound 50

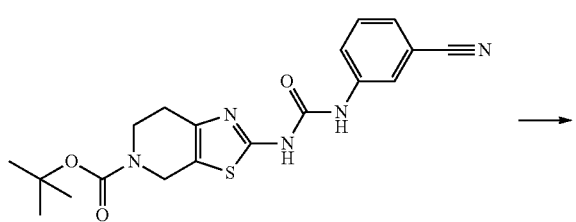

-continued

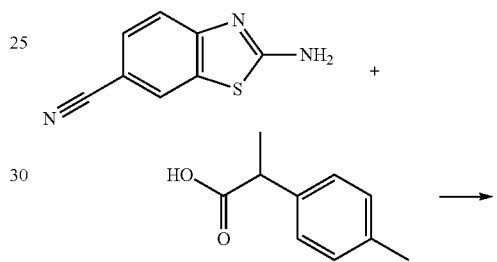

To a stirred solution of compound 39 (70 mg, 0.18 mmol) in $CH_2Cl_2$ (3 ml) was added TFA (0.10 ml, 1.3 mmol) at ambient temperature. After 3 h, additional TFA was added (0.10 ml) and the reaction was stirred overnight. The mixture was concentrated to give a white solid which was washed with EtOAc and dried on high vacuum (45 mg, 62%). LC/MS: M+1=300

Preparation of Compound 55

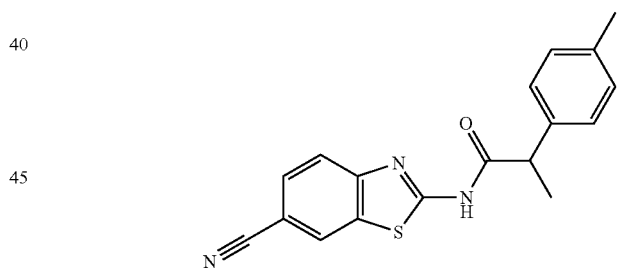

To a solution of 2-(p-tolyl)propanoic acid (100 mg, 0.61 mmole) in DOM (1.5 mL) was added oxalyl chloride (125 mg, 1.5 eq, 0.98 mmole) followed by DMF (1 drop). The resulting solution was stirred at room temperature for 1 hour, then concentrated to dryness under reduced pressure. The residue was dissolved in DCM (1.5 mL), 2-amino-6-cyano-benzonitrile (105 mg, 0.9 eq, 0.6 mmole) was added followed by triethylamine (135 mg, 2 eq, 1.34 mmole). The resulting solution was stirred at room temperature overnight. The mixture was concentrated under reduced pressure and purified by column chromatography eluting with 0-30% ethyl acetate in hexanes to give N-(6-cyano-1,3-benzothiazol-2-yl)-2-(p-tolyl)propenamide. (78 mg, 40%). LCMS (ESMS): m/z: 322 ($M^++1$)

Compounds 54, 56 and 57 were made by a procedure analogous to compound 55.

Preparation of Compound 61

The following two-step procedure was used for the preparation of Compound 61.

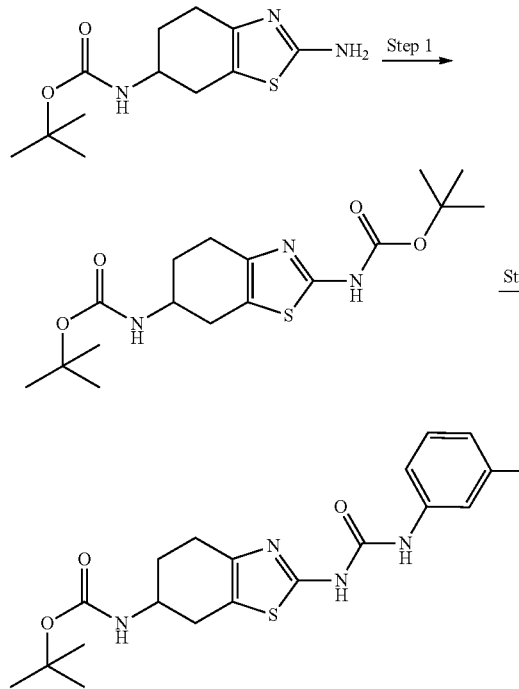

Step 1

To a cooled suspension (−10° C.) of 2,6-diamino-4,5,6,7-tetrahydrobezothiazole (0.5 g, 3.0 mmol) in THF (1 ml) was added a solution of di-tert-butyl decarbonate (0.64 g, 3.0 mmol) in THF (1 ml) in a dropwise manner. Upon complete addition the reaction was stirred overnight during which time it became homogenous. The reaction was poured into water and the product was extracted into EtOAc (3×). The combined organics were dried (MgSO$_4$), filtered and concentrated to give the crude product (tert-butyl N-[2-(tert-butoxycarbonylamino)-4,5,6,7-tetrahydro-1,3-benzothiazol-6-yl]carbamate) which was used without further purification. (0.79 g, 100%).

Step 2

To a solution of tert-butyl N-[2-(tert-butoxycarbonylamino)-4,5,6,7-tetrahydro-1,3-benzothiazol-6-yl]carbamate (200 mg, 0.54 mmol) in THF (8 mL) was added 3-cyanophenyl isocyanate (78 mg, 0.54 mmol) at room temperature. The solution was stirred at the same temperature for 24 hours. The solution was cooled under an ice-bath and the solid that precipitated out from the solution was collected by filtration. The solid was dried under vacuum to remove excess solvent. The solid was added to a boiling EtOH solution (10 mL) and was stirred at the same temperature for 30 minutes.

The solution was cooled down to room temperature and the solid was collected by filtration. The resulting solid was washed with cold EtOH (10 mL) and was dried under vacuum. The white solid was confirmed to be the title product (134 mg, 60%). LCMS (ESMS): m/z: 415 (M$^+$+1).

Preparation of Compound 69

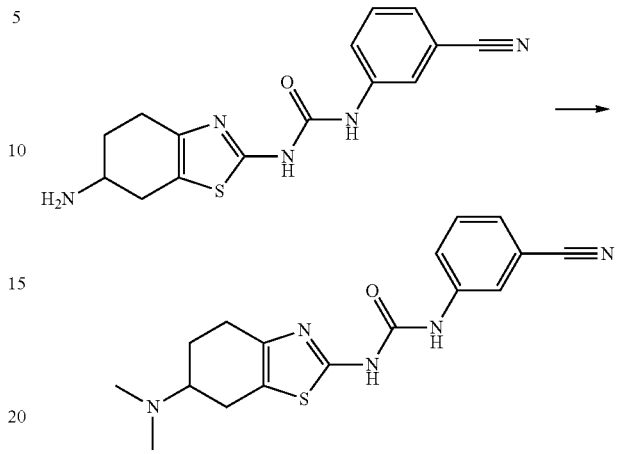

To a suspension of compound 67 (0.2 g, 0.6 mmol) in CH$_2$Cl$_2$ (5 ml) was added acetic acid (0.2 ml) and 37% formaldehyde (0.2 ml) at ambient temperature. After 0.5 h sodium borohydride (73 mg, 1.8 mmol) was added and the mixture was stirred overnight. The reaction was poured into NaHCO$_3$ (sat.) and the layers were separated. The aqueous phase was extracted with CH$_2$Cl$_2$ (3×) and the combined organics were dried (MgSO$_4$), filtered and concentrated. The crude was purified via column chromatography (SiO$_2$, 0-10% MeOH/DCM). Product-containing fractions were combined and concentrated and the resulting solid was treated with EtOH. The cloudy mixture was filtered, and the clear filtrate was concentrated to give the desired product (56 mg, 26%). LCMS (ESMS): m/z: 342 (M$^+$+1).

Preparation of Compound 84

The following two-step procedure was used for the preparation of Compound 84.

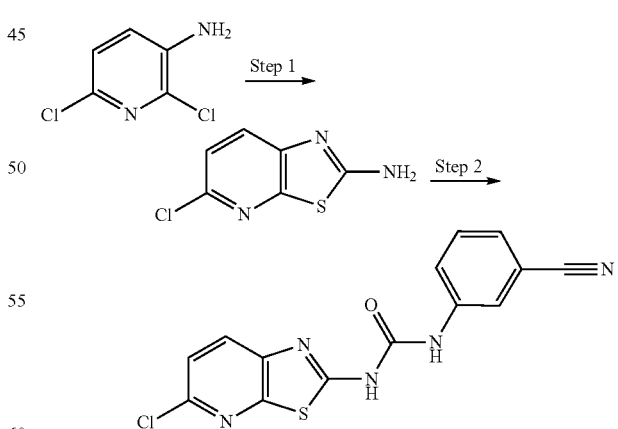

Step 1

To a solution of 3-amino-2,6-dichloropyridine (1.0 g, 6.1 mmol) and potassium thiocyanate (0.6 g, 6.1 mmol) in EtOH (15 ml) was added 12 N HCl (5 mL). The mixture was warmed to 100° C. for 18 h after which time the reaction was treated with another portion of potassium thiocyanate (1.2 g). After heating at 100° C. for 18 h the reaction was cooled to room temperature and was basified to pH=8 using 1N NaOH. The resulting precipitated product (5-chlorothiazolo[5,4-b]pyridin-2-amine) was collected via filtration and washed with water which was dried on high vacuum and used without further purification.

Step 2

To a solution of 5-chlorothiazolo[5,4-b]pyridin-2-amine (200 mg, 1.08 mmol) in THF (8 mL) was added 3-cyanophenyl isocyanate 156 mg, 1.08 mmol) at room temperature. The solution was stirred at the same temperature for 24 hours. The solution was cooled under an ice-bath and the solid that precipitated out from the solution was collected by filtration. The solid was dried under vacuum to remove excess solvent. The solid was added to a boiling EtOH solution (10 mL) and was stirred at the same temperature for 30 minutes. The solution was cooled down to room temperature and the solid was collected by filtration. The resulting solid was washed with cold EtOH (10 mL) and was dried under vacuum. The white solid was confirmed to be the title product (248 mg, 70%). LCMS (ESMS): m/z: 330 (M$^+$+1).

Preparation of Compound 90

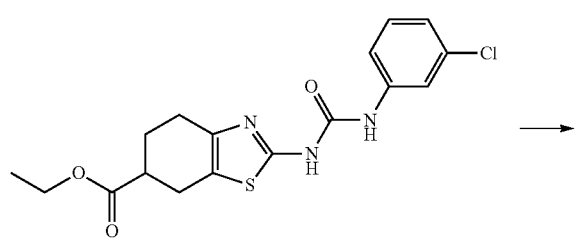

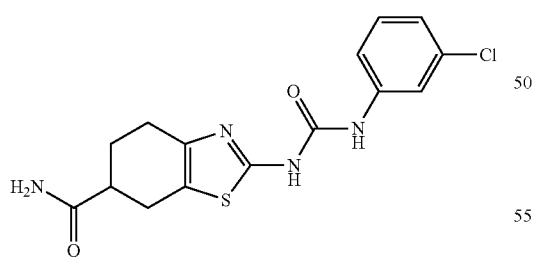

In a sealed tube were combined compound 80 (prepared according to the procedure of compound 24) (0.2 g, 0.5 mmol) and 7N NH$_3$ in MeOH (15 ml). After stirring for 4 days the reaction was warmed to 60° C. for 3 days. After this time the reaction was cooled and the solid was collected via filtration. The product was washed with MeOH to give the title product (2-[(3-chlorophenyl)carbamoylamino]-4,5,6,7-tetrahydro-1,3-benzothiazole-6-carboxamide) (140 mg, 80%). LCMS (ESMS): m/z: 352 (M$^+$+1).

Preparation of Compound 97

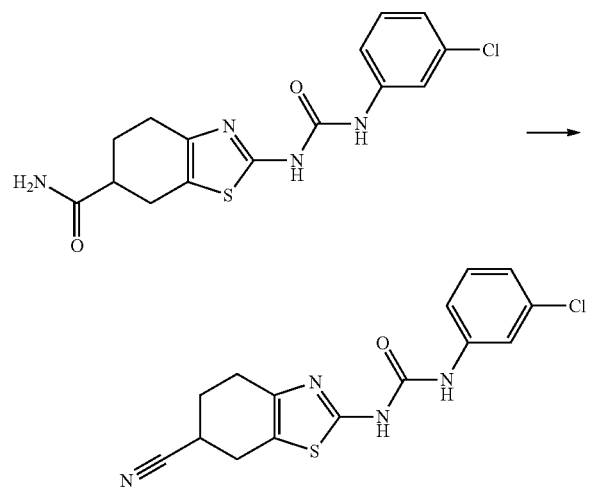

To a stirred solution of compound 90 (0.1 g, 0.3 mmol) in DMF (2 ml) was added thionyl chloride (0.9 mmol, 63 ul) at 0° C. After 2 h the reaction was quenched with NaHCO$_3$ (sat.) and stirred overnight. The solid was collected via filtration and purified via flash column chromatography (SiO2, 5-100% EtOAc/hexanes) to give the product. (24 mg, 25%) LCMS (ESMS): m/z: 334 (M$^+$+1).

Preparation of Compound 113

The following two-step procedure was used to prepare compound 113.

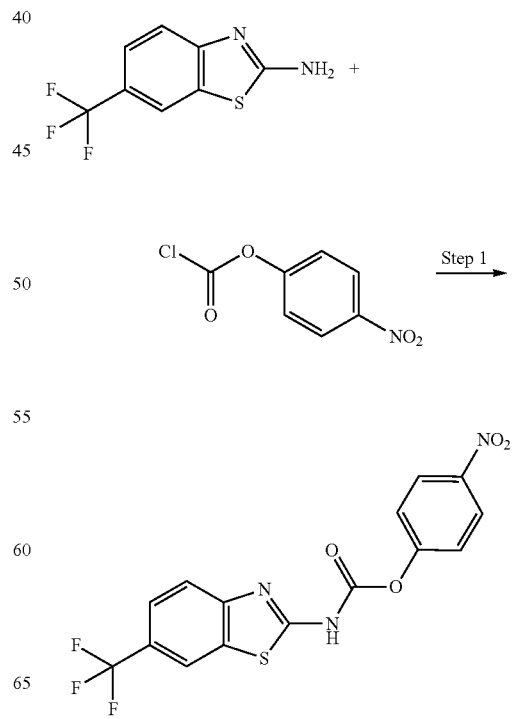

-continued

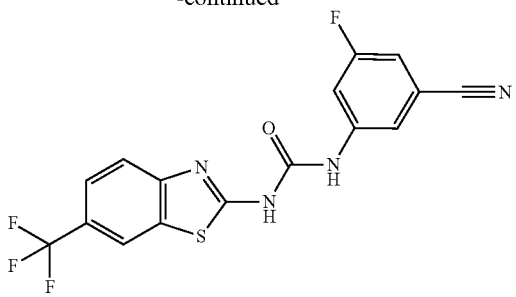

Step 1:

To a solution of 2-amino-6-trifluoromethylbenzothiazole (5 g, 22.9 mmole) in DCM (100 mL), was added a solution of 4-nitrophenylchloroformate (6.9 g, 1.5 eq, 34.3 mmole) in DCM (100 mL) dropwise from an addition funnel followed by a solution of pyridine (2.72 g, 1.5 eq, 34.3 mmole) in DCM (50 mL) dropwise from an addition funnel. The resulting mixture was stirred at room temperature overnight. The solids that precipitated out were collected by filtration and washed with DCM (2×50 mL). The solid was dried under vacuum to give 6.7 g of 4-nitrophenyl N-[6-(trifluoromethyl)-1,3-benzothiazol-2-yl]carbamate as a white solid.

Step 2:

To a solution of 4-nitrophenyl N-[6-(trifluoromethyl)-1,3-benzothiazol-2-yl]carbamate (400 mg, 1.04 mmole) in DMF (10 mL, 0.1 M) was added 3-amino-5-fluorobenzonitrile (142 mg, 1 eq, 1.04 mmole), the resulting solution was stirred at room temperature overnight. The mixture was poured into water (50 mL) and stirred for 1 hour, the resulting precipitate was collected by filtration and washed with water (2×20 mL). The solids were suspended in acetonitrile (5 mL) and water (5 mL) and stirred overnight. The solids were collected by filtration and washed with a 1:1 mixture of acetonitrile/water (2×10 mL), then dried in a vacuum oven at 50° C. to give 311 mg of 1-(3-cyano-5-fluorophenyl)-3-[6-(trifluoromethyl)-1,3-benzothiazol-2-yl] urea (311 mg, 78%). LCMS (ESMS): m/z: 381 (M$^+$+1). Compounds 45-47, 51, 68, 71, 81-83, 85-88, 91-96, 98, 99, 104-112, and 1114-123 were made by a procedure analogous to compound 113.

INCORPORATION BY REFERENCE

The entire disclosure of each of the patent documents, including certificates of correction, patent application documents, scientific articles, governmental reports, websites, and other references referred to herein is incorporated by reference herein in its entirety for all purposes. In case of a conflict in terminology, the present specification controls.

EQUIVALENTS

The invention can be embodied in other specific forms without departing from the spirit or essential characteristics thereof. The foregoing embodiments are to be considered in all respects illustrative rather than limiting on the invention described herein. In the various embodiments of the methods and systems of the present invention, where the term comprises is used with respect to the recited steps of the methods or components of the compositions, it is also contemplated that the methods and compositions consist essentially of, or consist of, the recited steps or components. Furthermore, it should be understood that the order of steps or order for performing certain actions is immaterial so long as the invention remains operable. Moreover, two or more steps or actions can be conducted simultaneously.

In the specification, the singular forms also include the plural forms, unless the context clearly dictates otherwise: Unless defined otherwise, all technical and scientific terms used herein have the same meaning as commonly understood by one of ordinary skill in the art to which this invention belongs. In the case of conflict, the present specification will control.

Furthermore, it should be recognized that in certain instances a composition can be described as being composed of the components prior to mixing, because upon mixing certain components can further react or be transformed into additional materials.

All percentages and ratios used herein, unless otherwise indicated, are by weight.

What is claimed is:

1. A compound having the following chemical structure or a pharmaceutically acceptable salt thereof:

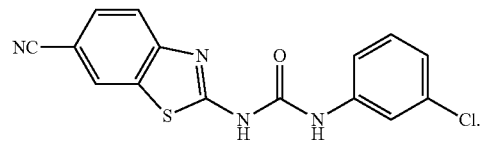 [SMILES: N#Cc1ccc2nc(NC(=O)Nc3cccc(Cl)c3)sc2c1]

2. A pharmaceutical composition comprising a compound according to claim 1 and a pharmaceutically acceptable carrier.

3. A method for treating a cancer selected from breast cancer, lung cancer, colorectal cancer, or glioblastoma in a mammal in need thereof comprising administering to the mammal a therapeutically effective amount of a compound having the following chemical structure or a pharmaceutically acceptable salt thereof:

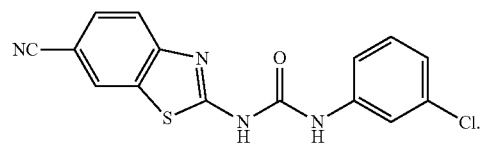

4. The method according to claim 3 wherein the mammal is a human.

* * * * *